(12) United States Patent
Balakin

(10) Patent No.: US 8,841,866 B2
(45) Date of Patent: Sep. 23, 2014

(54) CHARGED PARTICLE BEAM EXTRACTION METHOD AND APPARATUS USED IN CONJUNCTION WITH A CHARGED PARTICLE CANCER THERAPY SYSTEM

(76) Inventor: Vladimir Yegorovich Balakin, Protvino (RU)

( * ) Notice: Subject to any disclaimer, the term of this patent is extended or adjusted under 35 U.S.C. 154(b) by 887 days.

(21) Appl. No.: 12/994,126

(22) PCT Filed: May 21, 2009

(86) PCT No.: PCT/RU2009/000252
§ 371 (c)(1),
(2), (4) Date: Feb. 25, 2011

(87) PCT Pub. No.: WO2009/142550
PCT Pub. Date: Nov. 26, 2009

(65) Prior Publication Data
US 2011/0266455 A1    Nov. 3, 2011

Related U.S. Application Data

(60) Provisional application No. 61/209,529, filed on Mar. 9, 2009, provisional application No. 61/134,717, filed (Continued)

(30) Foreign Application Priority Data

Mar. 4, 2009  (WO) ................ PCT/RU2009/000105

(51) Int. Cl.
*H05H 7/00*  (2006.01)
*G21K 1/093*  (2006.01)
*G21K 1/087*  (2006.01)
*H05H 7/08*  (2006.01)
*H05H 7/10*  (2006.01)
*H05H 13/04*  (2006.01)
*G21K 1/14*  (2006.01)
*H05H 7/04*  (2006.01)
*A61N 5/10*  (2006.01)

(52) U.S. Cl.
CPC ................ *G21K 1/087* (2013.01); *G21K 1/093* (2013.01); *H05H 7/08* (2013.01); *H05H 7/10* (2013.01); *A61N 2005/1087* (2013.01); *H05H 13/04* (2013.01); *G21K 1/14* (2013.01); *H05H 7/04* (2013.01)

USPC ........................... 315/500; 315/503; 315/507

(58) Field of Classification Search
USPC ................................................ 315/500–507
See application file for complete search history.

(56) References Cited

U.S. PATENT DOCUMENTS 2,306,875 A    12/1942  Fremlin
2,533,688 A    12/1950  Quam
(Continued)

FOREIGN PATENT DOCUMENTS

CN    1178667    4/1998
CN    1242594    1/2000
(Continued)

OTHER PUBLICATIONS

Amaldi, et al ("A Hospital-Based Hadrontherapy Complex" Proceedings of EPAC 94, Jun. 27, 1994-Jul. 1, 1994, pp. 49-51, XP002552288, London England).*

(Continued)

*Primary Examiner* — Douglas W Owens
*Assistant Examiner* — Henry Luong
(74) *Attorney, Agent, or Firm* — Michael A. Glenn; Perkins Coie LLP

(57) ABSTRACT

The invention comprises a charged particle beam extraction method and apparatus used in conjunction with charged particle beam radiation therapy of cancerous tumors. The system uses a radio-frequency cavity system to induce betatron oscillation of a charged particle stream. Sufficient amplitude modulation of the charged particle stream causes the charged particle stream to hit a material, such as a foil. The foil decreases the energy of the charged particle stream, which decreases a radius of curvature of the charged particle stream in the synchrotron sufficiently to allow a physical separation of the reduced energy charged particle stream from the original charged particle stream. The physically separated charged particle stream is then removed from the system by use of an applied field and deflector.

33 Claims, 10 Drawing Sheets

Related U.S. Application Data on Jul. 14, 2008, provisional application No. 61/201,731, filed on Dec. 15, 2008, provisional application No. 61/201,728, filed on Dec. 15, 2008, provisional application No. 61/198,508, filed on Nov. 7, 2008, provisional application No. 61/189,815, filed on Aug. 25, 2008, provisional application No. 61/188,406, filed on Aug. 11, 2008, provisional application No. 61/197,971, filed on Nov. 3, 2008, provisional application No. 61/191,043, filed on Sep. 8, 2008, provisional application No. 61/192,237, filed on Sep. 17, 2008, provisional application No. 61/208,971, filed on Mar. 3, 2009, provisional application No. 61/199,405, filed on Nov. 17, 2008, provisional application No. 61/208,182, filed on Feb. 23, 2009, provisional application No. 61/188,407, filed on Aug. 11, 2008, provisional application No. 61/192,245, filed on Sep. 17, 2008, provisional application No. 61/190,613, filed on Sep. 2, 2008, provisional application No. 61/198,509, filed on Nov. 7, 2008, provisional application No. 61/190,546, filed on Sep. 2, 2008, provisional application No. 61/201,732, filed on Dec. 15, 2008, provisional application No. 61/199,404, filed on Nov. 17, 2008, provisional application No. 61/199,403, filed on Nov. 17, 2008, provisional application No. 61/055,395, filed on May 22, 2008, provisional application No. 61/134,718, filed on Jul. 14, 2008, provisional application No. 61/137,574, filed on Aug. 1, 2008, provisional application No. 61/189,017, filed on Aug. 15, 2008, provisional application No. 61/198,248, filed on Nov. 5, 2008, provisional application No. 61/203,308, filed on Dec. 22, 2008, provisional application No. 61/134,707, filed on Jul. 14, 2008, provisional application No. 61/055,409, filed on May 22, 2008, provisional application No. 61/205,362, filed on Jan. 21, 2009.

(56) References Cited

U.S. PATENT DOCUMENTS

| | | |
|---|---|---|
| 2,790,902 A | 4/1957 | Wright |
| 2,822,490 A | 2/1958 | Scag |
| 3,128,405 A | 4/1964 | Lambertson |
| 3,328,708 A | 6/1967 | Smith et al. |
| 3,412,337 A | 11/1968 | Lothrop |
| 3,461,410 A | 8/1969 | Beth |
| 3,655,968 A | 4/1972 | Moore et al. |
| 3,806,749 A | 4/1974 | Yntema |
| 3,867,705 A | 2/1975 | Hudson |
| 3,882,339 A | 5/1975 | Rate et al. |
| 3,906,280 A | 9/1975 | Andelfinger |
| 4,344,011 A | 8/1982 | Hayashi et al. |
| 4,442,355 A | 4/1984 | Tamura et al. |
| 4,607,380 A | 8/1986 | Oliver |
| 4,612,660 A | 9/1986 | Huang et al. |
| 4,622,687 A | 11/1986 | Whitaker et al. |
| 4,705,955 A | 11/1987 | Mileikowsky |
| 4,726,046 A | 2/1988 | Nunan |
| 4,730,353 A | 3/1988 | Ono |
| 4,868,844 A | 9/1989 | Nunan |
| 4,870,287 A | 9/1989 | Cole |
| 4,992,746 A * | 2/1991 | Martin ......................... 315/503 |
| H909 H | 4/1991 | Danby et al. |
| 5,017,789 A | 5/1991 | Young |
| 5,039,867 A | 8/1991 | Nishihara |
| 5,073,913 A | 12/1991 | Martin |
| 5,117,829 A | 6/1992 | Miller et al. |
| 5,168,241 A | 12/1992 | Hirota |
| 5,177,448 A | 1/1993 | Ikeguchi |
| 5,260,581 A | 11/1993 | Lesyna |
| 5,285,166 A | 2/1994 | Hiramoto |
| 5,349,198 A | 9/1994 | Takanaka |
| 5,363,008 A | 11/1994 | Hiramoto |
| 5,388,580 A | 2/1995 | Sullivan |
| 5,402,462 A | 3/1995 | Nobuta |
| 5,423,328 A | 6/1995 | Gavish |
| 5,440,133 A | 8/1995 | Moyers |
| 5,483,129 A | 1/1996 | Yamamoto |
| 5,511,549 A | 4/1996 | Legg |
| 5,538,494 A | 7/1996 | Matsuda |
| 5,568,109 A | 10/1996 | Takayama |
| 5,576,549 A | 11/1996 | Hell et al. |
| 5,585,642 A | 12/1996 | Britton |
| 5,600,213 A | 2/1997 | Hiramoto |
| 5,626,682 A | 5/1997 | Kobari |
| 5,633,907 A | 5/1997 | Gravelle |
| 5,659,223 A | 8/1997 | Goodman |
| 5,661,366 A | 8/1997 | Hirota |
| 5,668,371 A | 9/1997 | Deasy et al. |
| 5,698,954 A | 12/1997 | Hirota |
| 5,760,395 A | 6/1998 | Johnstone |
| 5,789,875 A | 8/1998 | Hiramoto |
| 5,818,058 A | 10/1998 | Nakanishi |
| 5,820,320 A | 10/1998 | Kobari |
| 5,825,845 A | 10/1998 | Blair |
| 5,854,531 A | 12/1998 | Young et al. |
| 5,866,912 A | 2/1999 | Slater |
| 5,895,926 A | 4/1999 | Britton |
| 5,907,595 A | 5/1999 | Sommerer |
| 5,917,293 A | 6/1999 | Saito |
| 5,949,080 A | 9/1999 | Ueda et al. |
| 5,969,367 A | 10/1999 | Hiramoto |
| 5,986,274 A | 11/1999 | Akiyama |
| 5,993,373 A | 11/1999 | Nonaka |
| 6,008,499 A | 12/1999 | Hiramoto |
| 6,034,377 A | 3/2000 | Pu |
| 6,057,655 A | 5/2000 | Jongen |
| 6,087,670 A * | 7/2000 | Hiramoto et al. ......... 250/492.3 |
| 6,087,672 A | 7/2000 | Matsuda |
| 6,148,058 A | 11/2000 | Dobbs |
| 6,207,952 B1 | 3/2001 | Kan |
| 6,218,675 B1 | 4/2001 | Akiyama |
| 6,236,043 B1 | 5/2001 | Tadokoro |
| 6,265,837 B1 | 7/2001 | Akiyama |
| 6,282,263 B1 | 8/2001 | Arndt |
| 6,292,538 B1 | 9/2001 | Hell et al. |
| 6,316,776 B1 | 11/2001 | Hiramoto |
| 6,322,249 B1 | 11/2001 | Wofford |
| 6,333,966 B1 | 12/2001 | Schoen |
| 6,335,535 B1 | 1/2002 | Miyake et al. |
| 6,339,635 B1 | 1/2002 | Schardt |
| 6,356,617 B1 | 3/2002 | Besch |
| 6,365,894 B2 | 4/2002 | Tadokoro |
| 6,403,967 B1 | 6/2002 | Chen et al. |
| 6,421,416 B1 | 7/2002 | Sliski |
| 6,433,336 B1 | 8/2002 | Jongen |
| 6,433,349 B2 | 8/2002 | Akiyama |
| 6,433,494 B1 | 8/2002 | Kulish |
| 6,437,513 B1 | 8/2002 | Stelzer |
| 6,444,990 B1 | 9/2002 | Morgan |
| 6,462,348 B1 | 10/2002 | Gelbart |
| 6,462,490 B1 | 10/2002 | Matsuda |
| 6,470,068 B2 | 10/2002 | Cheng |
| 6,472,834 B2 | 10/2002 | Hiramoto |
| 6,476,403 B1 | 11/2002 | Dolinskii |
| 6,545,436 B1 | 4/2003 | Gary |
| 6,560,354 B1 | 5/2003 | Maurer, Jr. |
| 6,580,084 B1 | 6/2003 | Hiramoto |
| 6,597,005 B1 | 7/2003 | Badura |
| 6,600,164 B1 | 7/2003 | Badura |
| 6,614,038 B1 | 9/2003 | Brand |
| 6,617,598 B1 | 9/2003 | Matsuda |
| 6,626,842 B2 | 9/2003 | Oka |
| 6,635,882 B1 | 10/2003 | Pavlovic et al. |
| 6,639,234 B1 | 10/2003 | Badura |
| 6,661,876 B2 | 12/2003 | Turner et al. |
| 6,670,618 B1 | 12/2003 | Hartmann |

(56) References Cited

U.S. PATENT DOCUMENTS

| | | |
|---|---|---|
| 6,683,318 B1 | 1/2004 | Haberer |
| 6,683,426 B1 | 1/2004 | Kleeven |
| 6,710,362 B2 | 3/2004 | Kraft |
| 6,717,162 B1 | 4/2004 | Jongen |
| 6,730,921 B2 | 5/2004 | Kraft |
| 6,736,831 B1 | 5/2004 | Hartmann |
| 6,745,072 B1 | 6/2004 | Badura |
| 6,774,383 B2 | 8/2004 | Norimine |
| 6,777,700 B2 | 8/2004 | Yanagisawa |
| 6,785,359 B2 | 8/2004 | Lemaitre |
| 6,787,771 B2 | 9/2004 | Bashkirov |
| 6,792,078 B2 | 9/2004 | Kato |
| 6,799,068 B1 | 9/2004 | Hartmann |
| 6,800,866 B2 | 10/2004 | Amemiya |
| 6,803,591 B2 | 10/2004 | Muramatsu et al. |
| 6,809,325 B2 | 10/2004 | Dahl |
| 6,819,743 B2 | 11/2004 | Kato |
| 6,822,244 B2 | 11/2004 | Beloussov |
| 6,823,045 B2 | 11/2004 | Kato |
| 6,838,676 B1 | 1/2005 | Jackson |
| 6,859,741 B2 | 2/2005 | Haberer |
| 6,873,123 B2 | 3/2005 | Marchand |
| 6,881,970 B2 | 4/2005 | Akiyama |
| 6,891,177 B1 | 5/2005 | Kraft |
| 6,897,451 B2 | 5/2005 | Kaercher |
| 6,900,446 B2 | 5/2005 | Akiyama |
| 6,903,351 B1 | 6/2005 | Akiyama |
| 6,903,356 B2 | 6/2005 | Muramatsu et al. |
| 6,931,100 B2 | 8/2005 | Kato |
| 6,936,832 B2 | 8/2005 | Norimine |
| 6,937,696 B1 | 8/2005 | Mostafavi |
| 6,953,943 B2 | 10/2005 | Yanagisawa |
| 6,979,832 B2 | 12/2005 | Yanagisawa |
| 6,984,835 B2 | 1/2006 | Harada |
| 6,992,312 B2 | 1/2006 | Yanagisawa |
| 7,006,594 B2 | 2/2006 | Chell et al. |
| 7,012,267 B2 | 3/2006 | Moriyama |
| 7,026,636 B2 | 4/2006 | Yanagisawa |
| 7,030,396 B2 | 4/2006 | Muramatsu |
| 7,045,781 B2 | 5/2006 | Adamec |
| 7,049,613 B2 | 5/2006 | Yanagisawa |
| 7,053,389 B2 | 5/2006 | Yanagisawa |
| 7,054,801 B2 | 5/2006 | Sakamoto |
| 7,058,158 B2 | 6/2006 | Sako |
| 7,060,997 B2 | 6/2006 | Norimine et al. |
| 7,071,479 B2 | 7/2006 | Yanagisawa |
| 7,081,619 B2 | 7/2006 | Bashkirov |
| 7,084,410 B2 | 8/2006 | Beloussov |
| 7,091,478 B2 | 8/2006 | Haberer |
| 7,102,144 B2 | 9/2006 | Matsuda |
| 7,109,505 B1 | 9/2006 | Sliski |
| 7,122,811 B2 | 10/2006 | Matsuda |
| 7,141,810 B2 | 11/2006 | Kakiuchi |
| 7,154,107 B2 | 12/2006 | Yanagisawa |
| 7,154,108 B2 | 12/2006 | Tadokoro |
| 7,173,264 B2 | 2/2007 | Moriyama |
| 7,173,265 B2 | 2/2007 | Miller |
| 7,193,227 B2 | 3/2007 | Hiramoto |
| 7,199,382 B2 | 4/2007 | Rigney |
| 7,208,748 B2 | 4/2007 | Sliski |
| 7,212,509 B1 | 5/2007 | Nagamine |
| 7,212,608 B2 | 5/2007 | Nagamine |
| 7,212,609 B2 | 5/2007 | Nagamine |
| 7,223,463 B2 | 5/2007 | Arakida |
| 7,227,161 B2 | 6/2007 | Matsuda |
| 7,247,869 B2 | 7/2007 | Tadokoro |
| 7,252,745 B2 | 8/2007 | Gorokhovsky |
| 7,259,529 B2 | 8/2007 | Tanaka |
| 7,262,424 B2 | 8/2007 | Moriyama |
| 7,274,018 B2 | 9/2007 | Adamec |
| 7,274,025 B2 | 9/2007 | Berdermann |
| 7,280,633 B2 | 10/2007 | Cheng |
| 7,297,967 B2 | 11/2007 | Yanagisawa |
| 7,301,162 B2 | 11/2007 | Matsuda |
| 7,307,264 B2 | 12/2007 | Brusasco |
| 7,310,404 B2 | 12/2007 | Tashiro |
| 7,315,606 B2 | 1/2008 | Tsujii |
| 7,319,231 B2 | 1/2008 | Moriyama |
| 7,345,291 B2 | 3/2008 | Kats |
| 7,345,292 B2 | 3/2008 | Moriyama |
| 7,349,522 B2 | 3/2008 | Yan et al. |
| 7,351,988 B2 | 4/2008 | Naumann |
| 7,355,189 B2 | 4/2008 | Yanagisawa |
| 7,356,112 B2 | 4/2008 | Brown |
| 7,368,740 B2 | 5/2008 | Beloussov |
| 7,372,053 B2 | 5/2008 | Yamashita |
| 7,381,979 B2 | 6/2008 | Yamashita |
| 7,385,203 B2 | 6/2008 | Nakayama |
| 7,394,082 B2 | 7/2008 | Fujimaki |
| 7,397,054 B2 | 7/2008 | Natori |
| 7,397,901 B1 | 7/2008 | Johnsen |
| 7,402,822 B2 | 7/2008 | Guertin |
| 7,402,823 B2 | 7/2008 | Guertin |
| 7,402,824 B2 | 7/2008 | Guertin |
| 7,402,963 B2 | 7/2008 | Sliski |
| 7,425,717 B2 | 9/2008 | Matsuda |
| 7,432,516 B2 | 10/2008 | Peggs |
| 7,439,528 B2 | 10/2008 | Nishiuchi |
| 7,446,490 B2 | 11/2008 | Jongen |
| 7,449,701 B2 | 11/2008 | Fujimaki |
| 7,456,415 B2 | 11/2008 | Yanagisawa |
| 7,456,591 B2 | 11/2008 | Jongen |
| 7,465,944 B2 | 12/2008 | Ueno |
| 7,476,883 B2 | 1/2009 | Nutt |
| 7,531,818 B2 | 5/2009 | Brahme |
| 7,555,103 B2 | 6/2009 | Johnsen |
| 7,560,717 B2 | 7/2009 | Matsuda |
| 7,576,342 B2 | 8/2009 | Hiramoto |
| 7,586,112 B2 | 9/2009 | Chiba |
| 7,589,334 B2 | 9/2009 | Hiramoto |
| 7,626,347 B2 | 12/2009 | Sliski |
| 7,634,057 B2 | 12/2009 | Ein-Gal |
| 7,659,521 B2 | 2/2010 | Pedroni |
| 7,668,585 B2 | 2/2010 | Green |
| 7,692,168 B2 | 4/2010 | Moriyama |
| 7,701,677 B2 | 4/2010 | Schultz |
| 7,709,818 B2 | 5/2010 | Matsuda |
| 7,718,982 B2 | 5/2010 | Sliski |
| 7,728,311 B2 | 6/2010 | Gall |
| 7,729,469 B2 | 6/2010 | Kobayashi |
| 7,741,623 B2 | 6/2010 | Sommer |
| 7,755,305 B2 | 7/2010 | Umezawa |
| 7,772,577 B2 | 8/2010 | Saito |
| 7,796,730 B2 | 9/2010 | Marash |
| 7,801,277 B2 | 9/2010 | Zou |
| 7,807,982 B2 | 10/2010 | Nishiuchi |
| 7,817,778 B2 | 10/2010 | Nord |
| 7,825,388 B2 | 11/2010 | Nihongi |
| 7,826,593 B2 | 11/2010 | Svensson |
| 7,834,336 B2 | 11/2010 | Boeh |
| 7,838,855 B2 | 11/2010 | Fujii |
| 7,848,488 B2 | 12/2010 | Mansfield |
| 7,860,216 B2 | 12/2010 | Jongen |
| 7,875,868 B2 | 1/2011 | Moriyama |
| 7,894,574 B1 | 2/2011 | Nord |
| 7,906,769 B2 | 3/2011 | Blasche |
| 7,919,765 B2 | 4/2011 | Timmer |
| 7,940,891 B2 | 5/2011 | Star-Lack |
| 7,953,205 B2 | 5/2011 | Balakin |
| 7,961,844 B2 | 6/2011 | Takeda |
| 7,977,656 B2 | 7/2011 | Fujimaki |
| 7,982,198 B2 | 7/2011 | Nishiuchi |
| 7,987,053 B2 | 7/2011 | Schaffner |
| 7,995,813 B2 | 8/2011 | Foshee |
| 8,003,964 B2 | 8/2011 | Stark |
| 8,009,804 B2 | 8/2011 | Siljamaki |
| 8,045,679 B2 | 10/2011 | Balakin |
| 8,093,564 B2 | 1/2012 | Balakin |
| 8,129,694 B2 | 3/2012 | Balakin |
| 8,129,699 B2 | 3/2012 | Balakin |
| 8,129,701 B2 | 3/2012 | Al-Sadah et al. |
| 8,144,832 B2 | 3/2012 | Balakin |
| 2002/0183667 A1 | 12/2002 | Kitadou et al. |
| 2003/0048080 A1 | 3/2003 | Amemiya et al. |

(56) References Cited

U.S. PATENT DOCUMENTS

| | | |
|---|---|---|
| 2003/0104207 A1 | 6/2003 | Arakida et al. |
| 2003/0163015 A1 | 8/2003 | Yanagisawa |
| 2003/0164459 A1 | 9/2003 | Schardt et al. |
| 2003/0188757 A1 | 10/2003 | Yanof et al. |
| 2004/0002641 A1 | 1/2004 | Sjogren et al. |
| 2004/0022361 A1 | 2/2004 | Lemaitre |
| 2004/0062354 A1 | 4/2004 | Kato et al. |
| 2004/0155206 A1 | 8/2004 | Marchand et al. |
| 2004/0162457 A1 | 8/2004 | Maggiore et al. |
| 2004/0184583 A1 | 9/2004 | Nagamine et al. |
| 2004/0218725 A1 | 11/2004 | Radley et al. |
| 2005/0017193 A1 | 1/2005 | Jackson |
| 2005/0134204 A1 | 6/2005 | Bechthold et al. |
| 2005/0161618 A1 | 7/2005 | Pedroni |
| 2005/0211905 A1 | 9/2005 | Stark |
| 2005/0226378 A1 | 10/2005 | Cocks et al. |
| 2005/0238134 A1 | 10/2005 | Brusasco |
| 2005/0258784 A1 | 11/2005 | Makita et al. |
| 2005/0269497 A1 | 12/2005 | Jongen |
| 2006/0050848 A1 | 3/2006 | Vilsmeier et al. |
| 2006/0076515 A1 | 4/2006 | Matsuda et al. |
| 2006/0106301 A1 | 5/2006 | Kats |
| 2006/0163495 A1 | 7/2006 | Hiramoto et al. |
| 2006/0171508 A1 | 8/2006 | Noda et al. |
| 2006/0255285 A1 | 11/2006 | Jongen et al. |
| 2007/0018121 A1 | 1/2007 | Leyman |
| 2007/0055124 A1 | 3/2007 | Viswanathan et al. |
| 2007/0093723 A1 | 4/2007 | Keall et al. |
| 2007/0121788 A1 | 5/2007 | Mildner et al. |
| 2007/0131876 A1 | 6/2007 | Brahme |
| 2007/0170994 A1 | 7/2007 | Peggs |
| 2007/0181815 A1 | 8/2007 | Ebstein |
| 2007/0225603 A1 | 9/2007 | Jackson |
| 2008/0023644 A1 | 1/2008 | Pedroni |
| 2008/0043916 A1 | 2/2008 | Lemaitre |
| 2008/0049896 A1 | 2/2008 | Kuduvalli et al. |
| 2008/0067413 A1 | 3/2008 | Nutt |
| 2008/0093567 A1 | 4/2008 | Gall |
| 2008/0139955 A1 | 6/2008 | Hansmann et al. |
| 2008/0191142 A1 | 8/2008 | Pedroni |
| 2008/0258084 A1 | 10/2008 | Platzgummer et al. |
| 2009/0086905 A1 | 4/2009 | Boyden et al. |
| 2009/0096179 A1 | 4/2009 | Stark |
| 2009/0122961 A1 | 5/2009 | Ohsawa |
| 2009/0140672 A1 | 6/2009 | Gall |
| 2009/0168960 A1 | 7/2009 | Jongen |
| 2009/0189095 A1 | 7/2009 | Flynn et al. |
| 2009/0190719 A1 | 7/2009 | Barschdorf et al. |
| 2009/0200483 A1 | 8/2009 | Gall |
| 2009/0236545 A1 | 9/2009 | Timmer |
| 2009/0283704 A1 | 11/2009 | Nishiuchi |
| 2009/0289194 A1 | 11/2009 | Saito |
| 2009/0304153 A1 | 12/2009 | Amelia |
| 2009/0309046 A1 | 12/2009 | Balakin |
| 2010/0001212 A1 | 1/2010 | Nishiuchi |
| 2010/0008468 A1 | 1/2010 | Balakin |
| 2010/0008469 A1 | 1/2010 | Balakin |
| 2010/0020937 A1 | 1/2010 | Hautmann et al. |
| 2010/0027745 A1 | 2/2010 | Balakin |
| 2010/0033115 A1 | 2/2010 | Cleland |
| 2010/0045213 A1 | 2/2010 | Sliski |
| 2010/0059688 A1 | 3/2010 | Claereboudt |
| 2010/0060209 A1 | 3/2010 | Balakin |
| 2010/0128846 A1 | 5/2010 | Balakin |
| 2010/0176309 A1 | 7/2010 | Mackie et al. |
| 2010/0230617 A1 | 9/2010 | Gall |
| 2010/0272241 A1 | 10/2010 | Amelia |
| 2010/0308235 A1 | 12/2010 | Sliski |
| 2011/0073778 A1 | 3/2011 | Natori |
| 2011/0089329 A1 | 4/2011 | Jongen |
| 2011/0118530 A1 | 5/2011 | Balakin |
| 2011/0118531 A1 | 5/2011 | Balakin |
| 2011/0127443 A1 | 6/2011 | Comer |
| 2011/0137159 A1 | 6/2011 | Jongen |
| 2011/0150180 A1 | 6/2011 | Balakin |
| 2011/0168903 A1 | 7/2011 | Kyele et al. |
| 2011/0180720 A1 | 7/2011 | Balakin |
| 2011/0182410 A1 | 7/2011 | Balakin |
| 2011/0186720 A1 | 8/2011 | Jongen |
| 2012/0143051 A1 | 6/2012 | Balakin |

FOREIGN PATENT DOCUMENTS

| | | |
|---|---|---|
| EP | 1683545 A2 | 7/2006 |
| GB | 1270619 | 4/1972 |
| JP | 62-87171 | 4/1987 |
| JP | H01-162199 | 6/1989 |
| JP | 03-075071 | 3/1991 |
| JP | 05-137806 | 6/1993 |
| JP | H05-200126 | 8/1993 |
| JP | 07-303710 | 11/1995 |
| JP | 9129151 | 5/1997 |
| JP | 11-057042 | 3/1999 |
| JP | 2921433 | 7/1999 |
| JP | 2000-030641 | 1/2000 |
| JP | 2000021597 | 1/2000 |
| JP | 2002-33275 | 1/2002 |
| JP | 2002-540581 | 11/2002 |
| JP | 2002-360543 | 12/2002 |
| JP | 2003-534066 | 11/2003 |
| JP | 2004357724 | 12/2004 |
| RU | 2149045 | 5/2000 |
| RU | 2149662 | 5/2000 |
| RU | 2006103781 | 9/2007 |
| WO | WO-99/53998 | 10/1999 |
| WO | WO-00/58991 A1 | 10/2000 |
| WO | WO-2005018734 | 3/2005 |
| WO | WO-2006094533 | 9/2006 |
| WO | WO-2007014026 | 2/2007 |
| WO | WO-2008002443 | 2/2008 |
| WO | WO-2008044194 | 4/2008 |

OTHER PUBLICATIONS

"Proton-Ion Medical Machine Study (PIMMS) Part II", European Organization for Nuclear Research CERN—PS Division, Jul. 27, 2000, pp. 1-352.

Arimoto, et al., "A Study of the PRISM-FFAG Magnet", Proc. Of Cyclotron 2004 Conference, Tokyo, Japan, Oct. 2004, 243-245, plus 30 page presentation.

Adams, et al., "Electrostatic cylinder lenses II: Three element einzel lenses", Journal of Physics E: Sci. Intr., vol. 5, No. 2, Feb. 1972, pp. 150-155.

Amaldi, U. et al., "A Hospital-Based Hadrontherapy Complex", Proceedings of EPAC '94, London, England, Jun. 1994, pp. 49-51.

Arimoto, et al., "A Study of the PRISM-FFAG Magnet", Proc. of Cyclotron 2004 Conference, Tokyo, Japan, Oct. 2004, pp. 243-245.

Biophysics Group, et al., "Design, construction and First Experiments of a Magnetic Scanning System for Therapy. Radiobiological Experiments on the Radiobiological Action of Carbon, Oxygen and Neon", GSI Report, Gesellschaft Fuer Schwerionenforschung MbH, vol. GSI-91-18, Jun. 1991, pp. 1-31.

Blackmore, et al., "Operation of the TRIUMF Proton Therapy Facility", Proc. of the 1997 Particle Accelerator Conference, vol. 3, Piscataway, NJ, USA, May 1997, pp. 3831-3833.

Bryant, P., "Proton-Ion Medical Machine Study (PIMMS) Part II", Proton-Ion Medical Machine Study: PIMMS, European Organisation for Nuclear Research CERN—PS Division, Geneva, Switzerland, Jul. 2000, pp. 23, 228, 289-290.

Craddock, M.K., "New Concepts in FFAG Design for Secondary Beam Facilities and other Applications", Proc. of 2005 Particle Accelerator Conference, Knoxville, TN, USA, May 2005, pp. 261-265.

Dzhelepov, et al., "Use of USSR proton accelerators for medical purposes", IEEE Transactions on Nuclear Science USA, vol. ns-20, No. 3, Jun. 1973, pp. 268-270.

Endo, et al., "Medical Synchrotron for Proton Therapy", Proc. of EPAC 88, Rome, Italy, Jun. 1988, pp. 1459-1461.

Franzke, et al., "Commissioning of the heavy ion storage ring ESR", Proc. of EPAC 90, Nice, France, Jun. 1990, pp. 46-48.

(56) References Cited

OTHER PUBLICATIONS

Johnstone, et al., "Tune-Stabilized Linear-Field FFAG for Carbon Therapy", Proc. of EPAC 2006, Edinburgh, Scotland, UK, Jun. 2006, Total of 3 Pages.

Kalnins, J.G., "The use of electric mutipole lenses for bending and focusing polar molecules with application to the design of a rotational-state separator", Proc. of PAC 2003, Portland, OR, USA, May 2003, pp. 2951-2953.

Kim, et al., "50MEV Proton Beam Test Facility for Low Flux Beam Utilization Studies of PEFP", Proceedings of APAC 2004, Gyeongju, Korea, Oct. 2005, pp. 441-443.

Lapostolle, P., "Introduction a la theorie des accelerateurs lineaires", CERN Yellow Books, CERN87-09, Geneva, Switzerland, Jul. 1987, pp. 4-5.

Li, Yulin, "A Thin Beryllium Injection Window for CESR-C", Proc. PAC '03, Portland, Oregon, USA, May 2001, pp. 2264-2266.

Noda, et al., "Performance of a respiration-gated beam control system for patient treatment", Proc. EPAC 96, Barcelona, Spain, Jun. 1996, pp. 2656-2658.

Noda, et al., "Slow beam extraction by a transverse RF field with AM and FM", Nuclear Instruments & Methods in Physics Research, Section-A: Accelerators, Spectrometers, Detectors and Associated Equipment, vol. A 374, Amsterdam, NL, May 1996, pp. 269-277.

Peters, J., "Negative ion sources for high energy accelerators (invited)", Review of Scientific Instruments, AIP, vol. 71, No. 2, Melville, NY, US, Feb. 2000, pp. 1069-1074.

Pohlit, W., "Optimization of Cancer Treatment with Accelerator Produced Radiations", Proc. EPAC '98, Stockholm, Sweden, Jun. 1998, pp. 192-194.

Saito, et al., "RF Accelerating System for a Compact Ion Synchrotron", Proc. of 2001 PAC, Chicago, USA, Jun. 2001, pp. 966-968.

Suda, et al., "Medical application of the positron emitter beam at HIMAC", Proc. of EPAC 2000, Vienna, Austria, Jun. 2000, pp. 2554-2556.

Tanigaki, et al., "Construction of FFAG Accelerators in KURRI for ADS Study", Proc. of 2005, Knoxville, TN, USA, May 2005, pp. 350-352.

Trbojevic, et al., "Design of a Non-Scaling FFAG Accelerator for Proton Therapy", Proc. of 2004 Cyclotron Conf., Tokyo, Japan, Oct. 2004, Total of 3 pages.

Winkler, et al., "Charge Exchange Extraction at the Experimental Storage Ring ESR at GSI", Proc. of EPAC 98, Stockholm Sweden, Jun. 1998, pp. 559-561.

Rigney, et al., "Patient Positioning System for Radiation Therapy System", Mexican patent application No. PA/a/2006/001581, Corresponds to WO2005018734, published Mar. 3, 2005, May 2006.

Sugai, I. et al., "Development of thick, long-lived carbon stripper foils for PSR of LANL", Nuclear Instruments & Methods in Physics Research, Section-A, vol. 362 No. 1, Aug. 1, 1995, pp. 70-76.

Huttel, "Materials for Accelerator Vacuum Systems", CERN Accelerator School Vacuum Technology; Scanticon Conference Center, Snekersten, Denmark, May 28, 1999; 26 pages.

\* cited by examiner

CHARGED PARTICLE BEAM EXTRACTION METHOD AND APPARATUS USED IN CONJUNCTION WITH A CHARGED PARTICLE CANCER THERAPY SYSTEM

CROSS REFERENCES TO RELATED APPLICATIONS

This application is a National Stage Entry and claims priority to PCT Application No. PCT/RU2009/000252, filed May 21, 2009, and claims the benefit of:

U.S. provisional patent application No. 61/055,395 filed May 22, 2008;
U.S. provisional patent application No. 61/137,574 filed Aug. 1, 2008;
U.S. provisional patent application No. 61/192,245 filed Sep. 17, 2008;
U.S. provisional patent application No. 61/055,409 filed May 22, 2008;
U.S. provisional patent application No. 61/203,308 filed Dec. 22, 2008;
U.S. provisional patent application No. 61/188,407 filed Aug. 11, 2008;
U.S. provisional patent application No. 61/209,529 filed Mar. 9, 2009;
U.S. provisional patent application No. 61/188,406 filed Aug. 11, 2008;
U.S. provisional patent application No. 61/189,815 filed Aug. 25, 2008;
U.S. provisional patent application No. 61/208,182 filed Feb. 23, 2009;
U.S. provisional patent application No. 61/201,731 filed Dec. 15, 2008;
U.S. provisional patent application No. 61/208,971 filed Mar. 3, 2009;
U.S. provisional patent application No. 61/205,362 filed Jan. 21, 2009;
U.S. provisional patent application No. 61/134,717 filed Jul. 14, 2008;
U.S. provisional patent application No. 61/134,707 filed Jul. 14, 2008;
U.S. provisional patent application No. 61/201,732 filed Dec. 15, 2008;
U.S. provisional patent application No. 61/198,509 filed Nov. 7, 2008;
U.S. provisional patent application No. 61/134,718 filed Jul. 14, 2008;
U.S. provisional patent application No. 61/190,613 filed Sep. 2, 2008;
U.S. provisional patent application No. 61/191,043 filed Sep. 8, 2008;
U.S. provisional patent application No. 61/192,237 filed Sep. 17, 2008,
U.S. provisional patent application No. 61/201,728 filed Dec. 15, 2008;
U.S. provisional patent application No. 61/190,546 filed Sep. 2, 2008;
U.S. provisional patent application No. 61/189,017 filed Aug. 15, 2008;
U.S. provisional patent application No. 61/198,248 filed Nov. 5, 2008;
U.S. provisional patent application No. 61/198,508 filed Nov. 7, 2008;
U.S. provisional patent application No. 61/197,971 filed Nov. 3, 2008;
U.S. provisional patent application No. 61/199,405 filed Nov. 17, 2008;
U.S. provisional patent application No. 61/199,403 filed Nov. 17, 2008;
U.S. provisional patent application No. 61/199,404 filed Nov. 17, 2008; and
claims priority to PCT patent application no. PCT/RU2009/00105, "Multi-Field Charged Particle Cancer Therapy Method and Apparatus", filed Mar. 4, 2009;

all of which are incorporated herein in their entirety by this reference thereto.

BACKGROUND OF THE INVENTION

1. Field of the Invention

This invention relates generally to treatment of solid cancers. More particularly, the invention relates to a charged particle beam extraction method and apparatus used in conjunction with radiation treatment of cancerous tumors.

2. Discussion of the Prior Art

Cancer

A tumor is an abnormal mass of tissue. Tumors are either benign or malignant. A benign tumor grows locally, but does not spread to other parts of the body. Benign tumors cause problems, because of their spread, as they press and displace normal tissues. Benign tumors are dangerous in confined places, such as the skull. A malignant tumor is capable of invading other regions of the body. Metastasis is cancer spreading by invading normal tissue and spreading to distant tissues.

Cancer Treatment

Several forms of radiation therapy exist for cancer treatment, including: brachytherapy, traditional electromagnetic X-ray therapy, and proton therapy.

Proton therapy systems typically include: a beam generator, an accelerator, and a beam transport system to move the resulting accelerated protons to a plurality of treatment rooms where the protons are delivered to a tumor in a patient's body. Proton therapy works by aiming energetic ionizing particles, such as protons accelerated with a particle accelerator, into a target tumor. These particles damage the DNA of cells, ultimately causing their death. Cancerous cells, because of their high rate of division and their reduced ability to repair damaged DNA, are particularly vulnerable to attacks on their DNA.

Due to their relatively enormous size, protons scatter less easily than X-rays in tissue and there is very little lateral dispersion. Hence, the proton beam stays focused on the tumor shape without much lateral damage to surrounding tissue. All protons of a given energy have a certain range, defined by the Bragg peak, and the dosage delivery to tissue ratio is at a maximum over just the last few millimeters of the particle's range. The penetration depth depends on the energy of the particles, which is directly related to the speed to which the particles were accelerated by the proton accelerator. The speed of the proton is adjustable to the maximum rating of the accelerator. It is therefore possible to focus the cell damage due to the proton beam at the very depth in the tissues where the tumor is situated. Tissues situated before the Bragg peak receive some reduced dose of radiation and tissues situated after the peak receive no radiation.

Synchrotrons

K. Hiramoto, et. al. "Accelerator System", U.S. Pat. No. 4,870,287 (Sep. 26, 1989) describes an accelerator system having a selector electromagnet for introducing an ion beam accelerated by pre-accelerators into either a radioisotope producing unit or a synchrotron.

K. Hiramoto, et. al. "Circular Accelerator, Method of Injection of Charged Particle Thereof, and Apparatus for Injection of Charged Particle Thereof", U.S. Pat. No. 5,789,875 (Aug. 4, 1998) and K. Hiramoto, et. al. "Circular Accelerator, Method of Injection of Charged Particle Thereof, and Apparatus for Injection of Charged Particle Thereof", U.S. Pat. No. 5,600,213 (Feb. 4, 1997) both describe a method and apparatus for injecting a large number of charged particles into a vacuum duct where the beam of injection has a height and width relative to a geometrical center of the duct.

Accelerator/Synchrotron

H. Tanaka, et. al. "Charged Particle Accelerator", U.S. Pat. No. 7,259,529 (Aug. 21, 2007) describe a charged particle accelerator having a two period acceleration process with a fixed magnetic field applied in the first period and a timed second acceleration period to provide compact and high power acceleration of the charged particles.

T. Haberer, et. al. "Ion Beam Therapy System and a Method for Operating the System", U.S. Pat. No. 6,683,318 (Jan. 27, 2004) describe an ion beam therapy system and method for operating the system. The ion beam system uses a gantry that has vertical deflection system and a horizontal deflection system positioned before a last bending magnet that result in a parallel scanning mode resulting from an edge focusing effect.

V. Kulish, et. al. "Inductional Undulative EH-Accelerator", U.S. Pat. No. 6,433,494 (Aug. 13, 2002) describe an inductive undulative EH-accelerator for acceleration of beams of charged particles. The device consists of an electromagnet undulation system, whose driving system for electromagnets is made in the form of a radio-frequency (RF) oscillator operating in the frequency range from about 100 KHz to 10 GHz.

K. Saito, et. al. "Radio-Frequency Accelerating System and Ring Type Accelerator Provided with the Same", U.S. Pat. No. 5,917,293 (Jun. 29, 1999) describe a radio-frequency accelerating system having a loop antenna coupled to a magnetic core group and impedance adjusting means connected to the loop antenna. A relatively low voltage is applied to the impedance adjusting means allowing small construction of the adjusting means.

J. Hirota, et. al. "Ion Beam Accelerating Device Having Separately Excited Magnetic Cores", U.S. Pat. No. 5,661,366 (Aug. 26, 1997) describe an ion beam accelerating device having a plurality of high frequency magnetic field inducing units and magnetic cores.

J. Hirota, et. al. "Acceleration Device for Charged Particles", U.S. Pat. No. 5,168,241 (Dec. 1, 1992) describe an acceleration cavity having a high frequency power source and a looped conductor operating under a control that combine to control a coupling constant and/or de-tuning allowing transmission of power more efficiently to the particles.

Magnet Shape

M. Tadokoro, et. al. "Electromagnetic and Magnetic Field Generating Apparatus", U.S. Pat. No. 6,365,894 (Apr. 2, 2002) and M. Tadokoro, et. al. "Electromagnetic and Magnetic Field Generating Apparatus", U.S. Pat. No. 6,236,043 (May 22, 2001) each describe a pair of magnetic poles, a return yoke, and exciting coils. The interior of the magnetic poles each have a plurality of air gap spacers to increase magnetic field strength.

Extraction

T. Nakanishi, et. al. "Charged-Particle Beam Accelerator, Particle Beam Radiation Therapy System Using the Charged-Particle Beam Accelerator, and Method of Operating the Particle Beam Radiation Therapy System", U.S. Pat. No. 7,122,978 (Oct. 17, 2006) describe a charged particle beam accelerator having an RF-KO unit for increasing amplitude of betatron oscillation of a charged particle beam within a stable region of resonance and an extraction quadrupole electromagnet unit for varying a stable region of resonance. The RE-KO unit is operated within a frequency range in which the circulating beam does not go beyond a boundary of stable region of resonance and the extraction quadrupole electromagnet is operated with timing required for beam extraction.

T. Haberer, et. al. "Method and Device for Controlling a Beam Extraction Raster Scan Irradiation Device for Heavy Ions or Protons", U.S. Pat. No. 7,091,478 (Aug. 15, 2006) describe a method for controlling beam extraction irradiation in terms of beam energy, beam focusing, and beam intensity for every accelerator cycle.

K. Hiramoto, et. al. "Accelerator and Medical System and Operating Method of the Same", U.S. Pat. No. 6,472,834 (Oct. 29, 2002) describe a cyclic type accelerator having a deflection electromagnet and four-pole electromagnets for making a charged particle beam circulate, a multi-pole electromagnet for generating a stability limit of resonance of betatron oscillation, and a high frequency source for applying a high frequency electromagnetic field to the beam to move the beam to the outside of the stability limit. The high frequency source generates a sum signal of a plurality of alternating current (AC) signals of which the instantaneous frequencies change with respect to time, and of which the average values of the instantaneous frequencies with respect to time are different. The system applies the sum signal via electrodes to the beam.

K. Hiramoto, et. al. "Synchrotron Type Accelerator and Medical Treatment System Employing the Same", U.S. Pat. No. 6,087,670 (Jul. 11, 2000) and K. Hiramoto, et. al. "Synchrotron Type Accelerator and Medical Treatment System Employing the Same", U.S. Pat. No. 6,008,499 (Dec. 28, 1999) describe a synchrotron accelerator having a high frequency applying unit arranged on a circulating orbit for applying a high frequency electromagnetic field to a charged particle beam circulating and for increasing amplitude of betatron oscillation of the particle beam to a level above a stability limit of resonance. Additionally, for beam ejection, four-pole divergence electromagnets are arranged: (1) downstream with respect to a first deflector; (2) upstream with respect to a deflecting electromagnet; (3) downstream with respect to the deflecting electromagnet; and (4) and upstream with respect to a second deflector.

K. Hiramoto, et. al. "Circular Accelerator and Method and Apparatus for Extracting Charged-Particle Beam in Circular Accelerator", U.S. Pat. No. 5,363,008 (Nov. 8, 1994) describe a circular accelerator for extracting a charged-particle beam that is arranged to: (1) increase displacement of a beam by the effect of betatron oscillation resonance; (2) to increase the betatron oscillation amplitude of the particles, which have an initial betatron oscillation within a stability limit for resonance; and (3) to exceed the resonance stability limit thereby extracting the particles exceeding the stability limit of the resonance.

K. Hiramoto, et. al. "Method of Extracting Charged Particles from Accelerator, and Accelerator Capable Carrying Out the Method, by Shifting Particle Orbit", U.S. Pat. No. 5,285,166 (Feb. 8, 1994) describe a method of extracting a charged particle beam. An equilibrium orbit of charged particles maintained by a bending magnet and magnets having multipole components greater than sextuple components is shifted by a constituent element of the accelerator other than these magnets to change the tune of the charged particles.

Beam Energy/Intensity

M. Yanagisawa, et. al. "Charged Particle Therapy System, Range Modulation Wheel Device, and Method of Installing Range Modulation Wheel Device", U.S. Pat. No. 7,355,189

(Apr. 8, 2008) and Yanagisawa, et. al. "Charged Particle Therapy System, Range Modulation Wheel Device, and Method of Installing Range Modulation Wheel Device", U.S. Pat. No. 7,053,389 (May 30, 2008) both describe a particle therapy system having a range modulation wheel. The ion beam passes through the range modulation wheel resulting in a plurality of energy levels corresponding to a plurality of stepped thicknesses of the range modulation wheel.

M. Yanagisawa, et. al. "Particle Beam Irradiation System and Method of Adjusting Irradiation Apparatus", U.S. Pat. No. 7,297,967 (Nov. 20, 2007); M. Yanagisawa, et. al. "Particle Beam Irradiation System and Method of Adjusting Irradiation Apparatus", U.S. Pat. No. 7,071,479 (Jul. 4, 2006); M. Yanagisawa, et. al. "Particle Beam Irradiation System and Method of Adjusting Irradiation Apparatus", U.S. Pat. No. 7,026,636 (Apr. 11, 2006); and M. Yanagisawa, et. al. "Particle Beam Irradiation System and Method of Adjusting Irradiation Apparatus", U.S. Pat. No. 6,777,700 (Aug. 17, 2004) all describe a scattering device, a range adjustment device, and a peak spreading device. The scattering device and range adjustment device are combined together and are moved along a beam axis. The spreading device is independently moved along the axis to adjust the degree of ion beam scattering. Combined, the devise increases the degree of uniformity of radiation dose distribution to a diseased tissue.

A. Sliski, et. al. "Programmable Particle Scatterer for Radiation Therapy Beam Formation", U.S. Pat. No. 7,208,748 (Apr. 24, 2007) describe a programmable pathlength of a fluid disposed into a particle beam to modulate scattering angle and beam range in a predetermined manner. The charged particle beam scatterer/range modulator comprises a fluid reservoir having opposing walls in a particle beam path and a drive to adjust the distance between the walls of the fluid reservoir under control of a programmable controller to create a predetermined spread out Bragg peak at a predetermined depth in a tissue. The beam scattering and modulation is continuously and dynamically adjusted during treatment of a tumor to deposit a dose in a targeted predetermined three dimensional volume.

M. Tadokoro, et. al. "Particle Therapy System", U.S. Pat. No. 7,247,869 (Jul. 24, 2007) and U.S. Pat. No. 7,154,108 (Dec. 26, 2006) each describe a particle therapy system capable of measuring energy of a charged particle beam during irradiation during use. The system includes a beam passage between a pair of collimators, an energy detector mounted, and a signal processing unit.

G. Kraft, et. al. "Ion Beam Scanner System and Operating Method", U.S. Pat. No. 6,891,177 (May 10, 2005) describe an ion beam scanning system having a mechanical alignment system for the target volume to be scanned and allowing for depth modulation of the ion beam by means of a linear motor and transverse displacement of energy absorption means resulting in depth-staggered scanning of volume elements of a target volume.

G. Hartmann, et. al. "Method for Operating an Ion Beam Therapy System by Monitoring the Distribution of the Radiation Dose", U.S. Pat. No. 6,736,831 (May 18, 2004) describe a method for operation of an ion beam therapy system having a grid scanner and irradiates and scans an area surrounding an isocentre. Both the depth dose distribution and the transverse dose distribution of the grid scanner device at various positions in the region of the isocentre are measured and evaluated.

Y. Jongen "Method for Treating a Target Volume with a Particle Beam and Device Implementing Same", U.S. Pat. No. 6,717,162 (Apr. 6, 2004) describes a method of producing from a particle beam a narrow spot directed towards a target volume, characterized in that the spot sweeping speed and particle beam intensity are simultaneously varied.

G. Kraft, et. al. "Device for Irradiating a Tumor Tissue", U.S. Pat. No. 6,710,362 (Mar. 23, 2004) describe a method and apparatus of irradiating a tumor tissue, where the apparatus has an electromagnetically driven ion-braking device in the proton beam path for depth-wise adaptation of the proton beam that adjusts both the ion beam direction and ion beam range.

K. Matsuda, et. al. "Charged Particle Beam Irradiation Apparatus", U.S. Pat. No. 6,617,598 (Sep. 9, 2003) describe a charged particle beam irradiation apparatus that increased the width in a depth direction of a Bragg peak by passing the Bragg peak through an enlarging device containing three ion beam components having different energies produced according to the difference between passed positions of each of the filter elements.

H. Stelzer, et. al. "Ionization Chamber for Ion Beams and Method for Monitoring the Intensity of an Ion Beam", U.S. Pat. No. 6,437,513 (Aug. 20, 2002) describe an ionization chamber for ion beams and a method of monitoring the intensity of an ion therapy beam. The ionization chamber includes a chamber housing, a beam inlet window, a beam outlet window, a beam outlet window, and a chamber volume filled with counting gas.

H. Akiyama, et. al. "Charged-Particle Beam Irradiation Method and System", U.S. Pat. No. 6,433,349 (Aug. 13, 2002) and H. Akiyama, et. al. "Charged-Particle Beam Irradiation Method and System", U.S. Pat. No. 6,265,837 (Jul. 24, 2001) both describe a charged particle beam irradiation system that includes a changer for changing energy of the particle and an intensity controller for controlling an intensity of the charged-particle beam.

Y. Pu "Charged Particle Beam Irradiation Apparatus and Method of Irradiation with Charged Particle Beam", U.S. Pat. No. 6,034,377 (Mar. 7, 2000) describes a charged particle beam irradiation apparatus having an energy degrader comprising: (1) a cylindrical member having a length; and (2) a distribution of wall thickness in a circumferential direction around an axis of rotation, where thickness of the wall determines energy degradation of the irradiation beam.

Dosage

K. Matsuda, et. al. "Particle Beam Irradiation System", U.S. Pat. No. 7,372,053 (Nov. 27, 2007) describe a particle beam irradiation system ensuring a more uniform dose distribution at an irradiation object through use of a stop signal, which stops the output of the ion beam from the irradiation device.

H. Sakamoto, et. al. "Radiation Treatment Plan Making System and Method", U.S. Pat. No. 7,054,801 (May 30, 2006) describe a radiation exposure system that divides an exposure region into a plurality of exposure regions and uses a radiation simulation to plan radiation treatment conditions to obtain flat radiation exposure to the desired region.

G. Hartmann, et. al. "Method For Verifying the Calculated Radiation Dose of an Ion Beam Therapy System", U.S. Pat. No. 6,799,068 (Sep. 28, 2004) describe a method for the verification of the calculated dose of an ion beam therapy system that comprises a phantom and a discrepancy between the calculated radiation dose and the phantom.

H. Brand, et. al. "Method for Monitoring the Irradiation Control of an Ion Beam Therapy System", U.S. Pat. No. 6,614,038 (Sep. 2, 2003) describe a method of checking a calculated irradiation control unit of an ion beam therapy system, where scan data sets, control computer parameters, measuring sensor parameters, and desired current values of scanner magnets are permanently stored.

T. Kan, et. al. "Water Phantom Type Dose Distribution Determining Apparatus", U.S. Pat. No. 6,207,952 (Mar. 27, 2001) describe a water phantom type dose distribution apparatus that includes a closed water tank, filled with water to the brim, having an inserted sensor that is used to determine an actual dose distribution of radiation prior to radiation therapy.

Respiration

K. Matsuda "Radioactive Beam Irradiation Method and Apparatus Taking Movement of the Irradiation Area Into Consideration", U.S. Pat. No. 5,538,494 (Jul. 23, 1996) describes a method and apparatus that enables irradiation even in the case of a diseased part changing position due to physical activity, such as breathing and heart beat. Initially, a position change of a diseased body part and physical activity of the patient are measured concurrently and a relationship therebetween is defined as a function. Radiation therapy is performed in accordance to the function.

Problem

There exists in the art of particle beam treatment of cancerous tumors in the body a need for efficient extraction of charged particles from a synchrotron of a charged particle therapy system. Further, there exists a need for extraction of charged particles at a specified energy, time, and/or intensity to yield a charged particle beam for efficient, precise, and accurate in-vivo treatment of a solid cancerous tumor with minimization of damage to surrounding healthy tissue in a patient.

SUMMARY OF THE INVENTION

The invention comprises a charged particle beam extraction method and apparatus used in conjunction with charged particle beam radiation therapy of cancerous tumors.

DETAILED DESCRIPTION OF THE INVENTION

The invention comprises a charged particle beam extraction method and apparatus used in conjunction with charged particle beam radiation therapy of cancerous tumors.

Accurate and precise delivery of protons to a tumor in body tissue is critical in charged particle beam therapy. Herein, extraction of a charged particle beam from a synchrotron is described as part of a charged particle cancer tumor therapy system. The system uses a radio-frequency (RF) cavity system to induce betatron oscillation of a charged particle stream. Sufficient amplitude modulation of the charged particle stream causes the charged particle stream to hit a material, such as a foil. The foil decreases the energy of the charged particle stream, which decreases a radius of curvature of the charged particle stream in the synchrotron sufficiently to allow a physical separation of the reduced energy charged particle stream from the original charged particle stream. The physically separated charged particle stream is then removed from the system by use of an applied field and deflector. The extraction system is further described, infra.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. The techniques described herein are equally applicable to any charged particle beam system.

Figure 1:
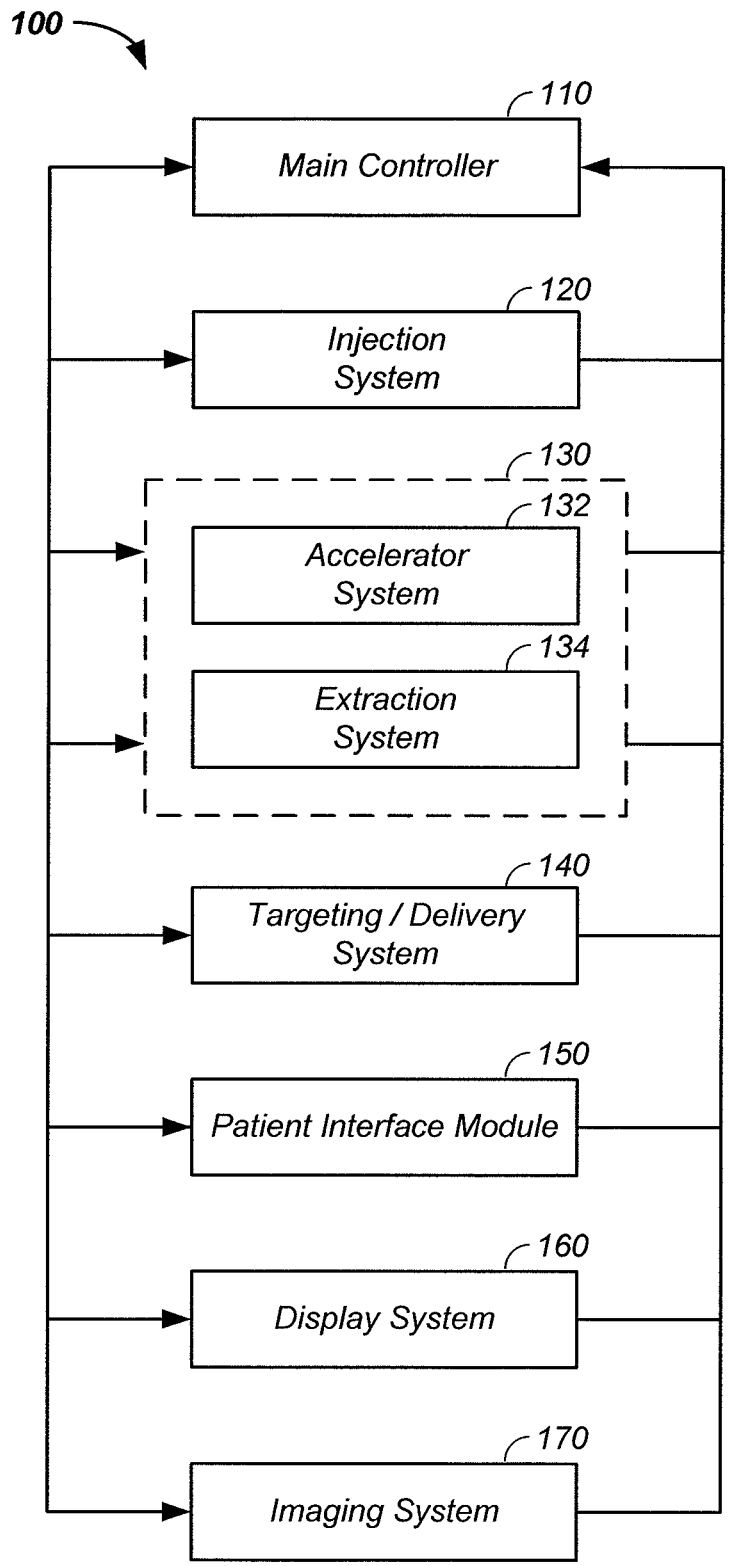
FIG. 1 illustrates sub-system connections of a particle beam therapy system.

Referring now to FIG. 1, a charged particle beam system 100 is illustrated. A charged particle beam, preferably comprises a number of subsystems including any of: a main controller 110; an injection system 120; a synchrotron 130 that typically includes: (1) an accelerator system 132 and (2) an extraction system 134; a targeting/delivery system 140; a patient interface module 150; a display system 160; and/or an imaging system 170.

In one embodiment, one or more of the subsystems are stored on a client. The client is a computing platform configured to act as a client device, e.g. a personal computer, a digital media player, a personal digital assistant, etc. The client comprises a processor that is coupled to a number of external or internal inputting devices; e.g. a mouse, a keyboard, a display device, etc. The processor is also coupled to an output device, e.g. a computer monitor to display information. In one embodiment, the main controller 110 is the processor. In another embodiment, the main controller 110 is a set of instructions stored in memory that is carried out by the processor.

The client includes a computer-readable storage medium, i.e. memory. The memory includes, but is not limited to, an electronic, optical, magnetic, or another storage or transmission device capable of coupling to a processor, e.g. such as a processor in communication with a touch-sensitive input device, with computer-readable instructions. Other examples of suitable media include, for example, flash drive, CD-ROM, read only memory (ROM), random access memory (RAM), application-specific integrated circuit (ASIC), DVD, magnetic disk, memory chip, etc. The processor executes a set of computer-executable program code instructions stored in the memory. The instructions may comprise code from any computer-programming language, including, for example, C, C++, C#, Visual Basic, Java, and JavaScript.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 then optionally controls the injection system 120 to inject a proton into a synchrotron 130. The synchrotron typically contains at least an accelerator system 132 and an extraction system 134. The main controller preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the targeting/delivery system 140 to the patient interface module 150. One or more components of the patient interface module 150 are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path; however, cyclotrons are alternatively used, albeit with their inherent limitations of energy, intensity, and extraction control. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central point or region.

Figure 2:
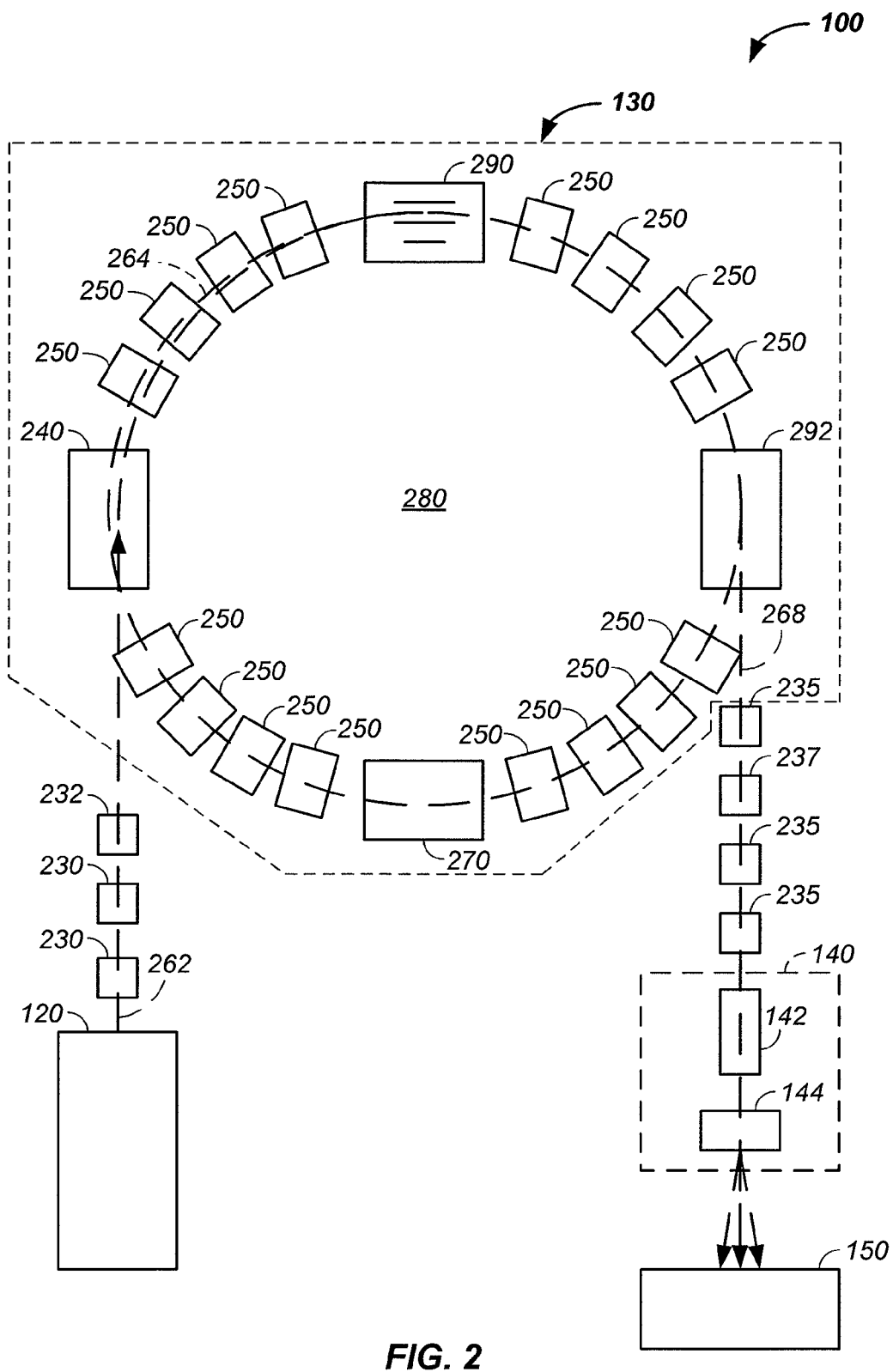
FIG. 2 illustrates a synchrotron.

Referring now to FIG. 2, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending magnets, dipole magnets, or circulating magnets 250 are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of the inflector/deflector system 290 is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path 268 into the scanning/targeting/delivery system 140. Two components of a scanning system 140 or targeting system typically include a first axis control 142, such as a vertical control, and a second axis control 144, such as a horizontal control. In one embodiment, the first axis control 142 allows for about 100 mm of vertical or y-axis scanning of the proton beam 268 and the second axis control 144 allows for about 700 mm of horizontal or x-axis scanning of the proton beam 268. A nozzle system is used for imaging the proton beam and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations. The above listed elements are further described, infra.

Ion Beam Generation System

An ion beam generation system generates a negative ion beam, such as a hydrogen anion or H⁻ beam; preferably focuses the negative ion beam; converts the negative ion beam to a positive ion beam, such as a proton or H⁺ beam; and injects the positive ion beam 262 into the synchrotron 130. Portions of the ion beam path are preferably under partial vacuum.

Synchrotron

Herein, the term synchrotron is used to refer to a system maintaining the charged particle beam in a circulating path. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central point or region 280.

Circulating System

The synchrotron 130 preferably comprises a combination of straight sections and ion beam turning sections. Hence, the circulating path of the protons is not circular in a synchrotron, but is rather a polygon with rounded corners.

In one illustrative embodiment, the synchrotron 130, which as also referred to as an accelerator system, has four straight elements and four turning sections. Examples of straight sections include the: inflector 240, accelerator 270, extraction system 290, and deflector 292. Along with the four straight sections are four ion beam turning sections, which are also referred to as magnet sections or turning sections. For example, a turning section is a set of about 2, 4, 6, or 8 turning magnets 250. Turning sections are further described, infra.

Referring still to FIG. 2, an exemplary synchrotron is illustrated. In this example, protons delivered along the initial proton beam path 262 are inflected into the circulating beam path with the inflector 240 and after acceleration are extracted via a deflector 292 to the beam transport path 268. In this example, the synchrotron 130 comprises four straight sections and four bending or turning sections where each of the four turning sections use one or more magnets to turn the proton beam about ninety degrees. As is further described, infra, the ability to closely space the turning sections and efficiently turn the proton beam results in shorter straight sections. Shorter straight sections allows for a synchrotron design without the use of focusing quadrupoles in the circulating beam path of the synchrotron. The removal of the focusing quadrupoles from the circulating proton beam path results in a more compact design. In this example, the illustrated synchrotron has about a five meter diameter versus eight meter and larger cross-sectional diameters for systems using a quadrupole focusing magnet in the circulating proton beam path.

Additional description of the first bending or turning section between injector magnet 240 and inflector/deflector system 290 is provided. Additional turning sections are (1) from the inflector/deflector system 290 to the Lamberson extraction magnet 292; (2) from the Lamberson extraction magnet 292 to the accelerator 270; and (3) from the accelerator 270 to the injector magnet 240. Each of the turning sections preferably comprise multiple magnets, such as about 2, 4, 5, 8, 10, or 12 magnets. In this example, four turning magnets or circulating magnets 250 in the first turning section 920 are used to illustrate key principles, which are the same regardless of the number of magnets in a turning section.

Turning Magnet Focusing Geometry

Figure 3:
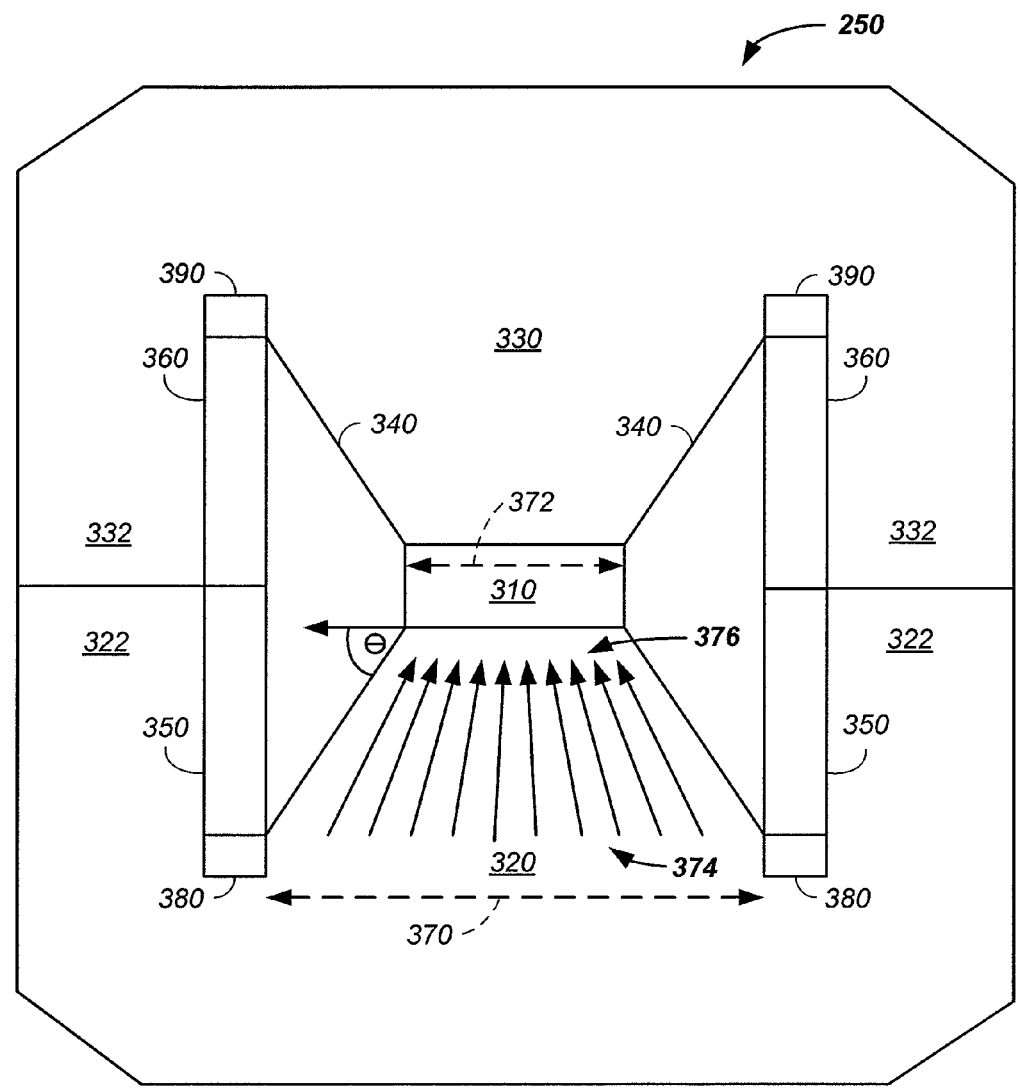
FIG. 3 illustrates a turning magnet within the synchrotron.

Referring now to FIG. 3, a cross section of a single turning magnet 250 is provided. The turning section includes a gap 310 through which protons circulate. The magnet assembly has a first magnet 320 and a second magnet 330. A magnetic field induced by coils runs between the first magnet 320 to the second magnet 330 across the gap 310. Return magnetic fields run through a first yoke 322 and second yoke 332. The magnetic field is created using a first winding coil 350 and a second winding coil 360. Isolating or concentrating gaps 340, such as air gaps, isolate the iron based yokes from the gap 310. The gap 310 is approximately flat to yield a uniform magnetic field across the gap 310. As illustrated, the first magnet 320 preferably contains an initial cross sectional distance 370 of the iron based core. The contours of the magnetic field are shaped by the magnets 320, 330 and the yokes 322, 332 from a first cross sectional distance or area 374 to a second cross sectional distance or area 376. For example, the first cross-sectional distance is about 15 cm and the second cross-section distance is about 10 cm. In a second example, the second cross section distance is less than seventy percent of the first cross-section distance. In these examples, the core tapers to a second cross sectional distance 372 with an angle theta, θ. As described, supra, the magnetic field in the magnet preferentially stays in the iron based core as opposed to the isolating gaps 340. As the cross-sectional distance decreases from the initial cross sectional distance 370 to the final cross-sectional distance 372, the magnetic field concentrates. The angle theta results in an amplification of the magnetic field in going from the longer distance 370 to the smaller distance 372. The concentration of the magnetic field is illustrated by representing an initial density of magnetic field vectors in the initial cross section 370 to a concentrated density of magnetic field vectors in the final cross section 372. The concentration of the magnetic field due to the geometry of the turning magnets results in fewer winding coils 350, 360 being required and also a smaller power supply to the winding coils 350, 360 being required.

Turning Magnet Correction Coils

Still referring to FIG. 3, optional correction coils 380, 390 are illustrated that are used to correct the strength of one or more turning magnets. The correction coils 380, 390 supplement the winding coils 350, 360. The correction coil power supplies typically operate at a fraction of the power required compared to the winding coil power supplies, such as about 1, 2, 3, 5, 7, or 10 percent of the power and more preferably about 1 or 2 percent of the power used with the winding coils 350, 360. The smaller operating power applied to the correction coils 380, 390 allows for more accurate and/or precise control of the correction coils. The correction coils 380, 390 are used to adjust for imperfection in the turning magnets 250. Optionally, separate correction coils are used for each turning magnet allowing individual tuning of the magnetic field for each turning magnet, which eases quality requirements in the manufacture of each turning magnet.

The winding coils preferably cover 1, 2, or 4 turning magnets 250. One or more high precision magnetic field sensors are placed into the synchrotron and are used to measure the magnetic field at or near the proton beam path. For example, the magnetic sensors are optionally placed between turning magnets and/or within a turning magnet, such as at or near the gap 310 or at or near the magnet core or yoke. The sensors are part of a feedback system to the correction coils, which is optionally run by the main controller. Thus, the system preferably stabilizes the magnetic field in the synchrotron elements rather than stabilizing the current applied to the magnets. Stabilization of the magnetic field allows the synchrotron to come to a new energy level quickly. This allows the system to be controlled to an operator or algorithm selected energy level with each pulse of the synchrotron and/or with each breath of the patient.

Turning Magnets Beveled Edges

The ends of a single bending or turning magnet are preferably beveled. Beveling the edge of the turning magnet 250 focuses the proton beam. Multiple turning magnets provide multiple magnet edges that each have edge focusing effects in the synchrotron 130. For example, if four magnets are used in a turning section of the synchrotron, then for a single turning section there are eight possible edge focusing effect surfaces, two edges per magnet. The eight focusing surfaces yield a smaller cross-sectional beam size, which allows the use of a smaller gap. For a synchrotron 130 having four turning sections, where each turning sections has four turning magnets and each turning magnet has two focusing edges, a total of thirty-two focusing edges exist for each orbit of the protons in the circulating path of the synchrotron 130. Similarly, if 2, 6, or 8 magnets are used in a given turning section, or if 2, 3, 5, or 6 turning sections are used, then the number of edge focusing surfaces expands or contracts according to equation 1.

$$TFE = NTS * \frac{M}{NTS} * \frac{FE}{M} \qquad \text{(eq. 1)}$$

where TFE is the number of total focusing edges, NTS is the number of turning sections, M is the number of magnets, and FE is the number of focusing edges. Naturally, not all magnets are necessarily beveled and some magnets are optionally beveled on only one edge.

In various embodiments of the system described herein, the synchrotron has any combination of:
  at least 4 and preferably 6, 8, 10, or more edge focusing edges per 90 degrees of turn of the charged particle beam in a synchrotron having four turning sections;
  at least about 16 and preferably about 24, 32, or more edge focusing edges per orbit of the charged particle beam in the synchrotron;
  only 4 turning sections where each of the turning sections includes at least 4 and preferably 8 edge focusing edges;

an equal number of straight sections and turning sections;
exactly 4 turning sections;
at least 4 focusing edges per turning section;
no quadrupoles in the circulating path of the synchrotron;
a rounded corner rectangular polygon configuration;
a circumference of less than 60 meters;
a circumference of less than 60 meters and 32 edge focusing surfaces; and/or;
any of about 8, 16, 24, or 32 non-quadrupole magnets per circulating path of the synchrotron, where the non-quadrupole magnets include edge focusing edges.

Proton Beam Extraction

Figure 4:
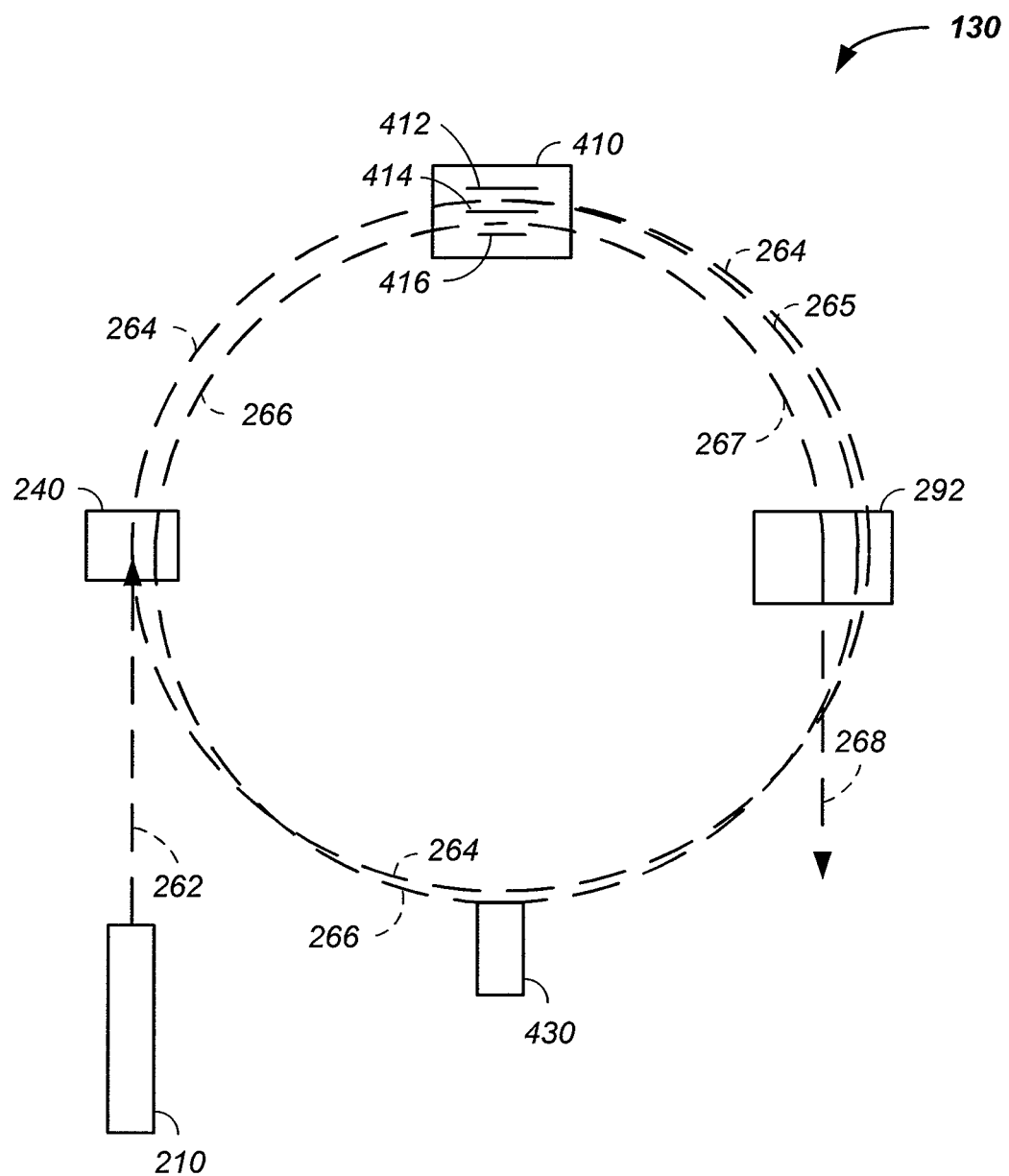
FIG. 4 illustrates a particle beam extraction system.

Referring now to FIG. 4, an exemplary proton extraction process from the synchrotron 130 is illustrated. For clarity, FIG. 4 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path 264, which is maintained with a plurality of turning magnets 250. The circulating path is referred to herein as an original central beamline 264. The protons repeatedly cycle around a central point in the synchrotron 280. The proton path traverses through an RF cavity system 410. To initiate extraction, an RF field is applied across a first blade 412 and a second blade 414, in the RF cavity system 410. The first blade 412 and second blade 414 are referred to herein as a first pair of blades.

In the proton extraction process, an RF voltage is applied across the first pair of blades, where the first blade 412 of the first pair of blades is on one side of the circulating proton beam path 264 and the second blade 414 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The applied RF field is timed to apply outward or inward movement to a given band of protons circulating in the synchrotron accelerator. Each orbit of the protons is slightly more off axis compared to the original circulating beam path 264. Successive passes of the protons through the RF cavity system are forced further and further from the original central beamline 264 by altering the direction and/or intensity of the RF field with each successive pass of the proton beam through the RF field.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons.

The process of timing the RF field to a given proton beam within the RF cavity system is repeated thousands of times with successive passes of the protons being moved approximately one micrometer further off of the original central beamline 264. For clarity, the approximately 1000 changing beam paths with each successive path of a given band of protons through the RF field are illustrated as the altered beam path 265.

With a sufficient sine wave betatron amplitude, the altered circulating beam path 265 touches a material 430, such as a foil or a sheet of foil. The foil is preferably a lightweight material, such as beryllium, a lithium hydride, a carbon sheet, or a material of low nuclear charge. A material of low nuclear charge is a material composed of atoms consisting essentially of atoms having six or fewer protons. The foil is preferably about 10 to 150 microns thick, is more preferably 30 to 100 microns thick, and is still more preferably 40-60 microns thick. In one example, the foil is beryllium with a thickness of about 50 microns. When the protons traverse through the foil, energy of the protons is lost and the speed of the protons is reduced. Typically, a current is also generated, described infra. Protons moving at a slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 430 is optionally adjusted to created a change in the radius of curvature, such as about ½, 1, 2, 3, or 4 mm less than the last pass of the protons 265 or original radius of curvature 264. Protons moving with the smaller radius of curvature travel between a second pair of blades 414, 416. The second pair of blades 414, 416 is also referred to as a pair of extraction blades.

In one case, the second pair of blades is physically distinct and/or are separated from the first pair of blades. In a second case, one of the first pair of blades is also a member of the second pair of blades. For example, the second pair of blades is the second blade 414 and a third blade 416 in the RF cavity system 410. A high voltage DC signal, such as about 0.5, 1, 2, 3, 4, or 5 kV, is then applied across the second pair of blades, which directs the protons out of the synchrotron through a deflector 292, such as a Lamberson magnet, into a transport path 268.

EXAMPLE I

In a first example, protons are extracted from a synchrotron by slowing the protons with a foil. Initially, an RF signal is applied across a proton path, such as through two metal elements where one metallic element is on a first side of a cyclic proton path in the synchrotron and a second metallic element is on an opposite side of the proton path. An RF voltage is applied across the two metal elements. The applied voltage is modulated or frequency modulated to induce an oscillation in the path of the protons. The oscillation forces a portion of the proton beam through a foil. In this case, the foil is a beryllium material of about fifty microns in thickness. The electrons on the foil slow the protons resulting in a beam path having a smaller average diameter compared to protons repeatedly cycling in the synchrotron. The protons having the smaller average diameter beam path traverse a high DC voltage field, which directs the protons out of the synchrotron or into a Lamberson magnet directing the protons out of the synchrotron.

EXAMPLE II

Still referring to FIG. 4, an exemplary synchrotron 130 is illustrated: A set of magnets control protons in the synchrotron in a repeated cyclic path 264 having a first radius of curvature. Protons in the first path traverse between a first pair of metal plates 412, 414 having an AC frequency voltage applied across the two metal plates. The AC voltage induces an oscillation on some of the protons causing them to pass through a foil material 430 that reduces the speed of the protons. The protons moving at a slower speed have a reduced radius of curvature path 266. The protons having the reduced radius of curvature then pass through a DC field, such as a high voltage field between a second pair of metal plates 414, 416, which directs the protons along a new path. The new path 266 optionally traverses another magnetic field, such as that of a Lamberson magnet, that directs the protons away from the synchrotron.

Generally, the extraction process takes a proton circulating in a synchrotron and slows the proton by passing the proton through a foil. The circulating proton has a first radius of curvature associated with the energy of the circulating proton and the applied magnetic fields of the turning magnets. The protons passing through the foil have less energy resulting in a second radius of curvature that is less than the first radius of curvature. Hence, the protons are extracted toward the center of the synchrotron relative to the circulating proton beam path. The smaller radius of curvature slowed protons, after passing through the foil, are kicked out of the synchrotron by application of a field between the second and third plates and via use of a deflector, such as a Lamberson deflector.

Intensity Control

Figure 5:
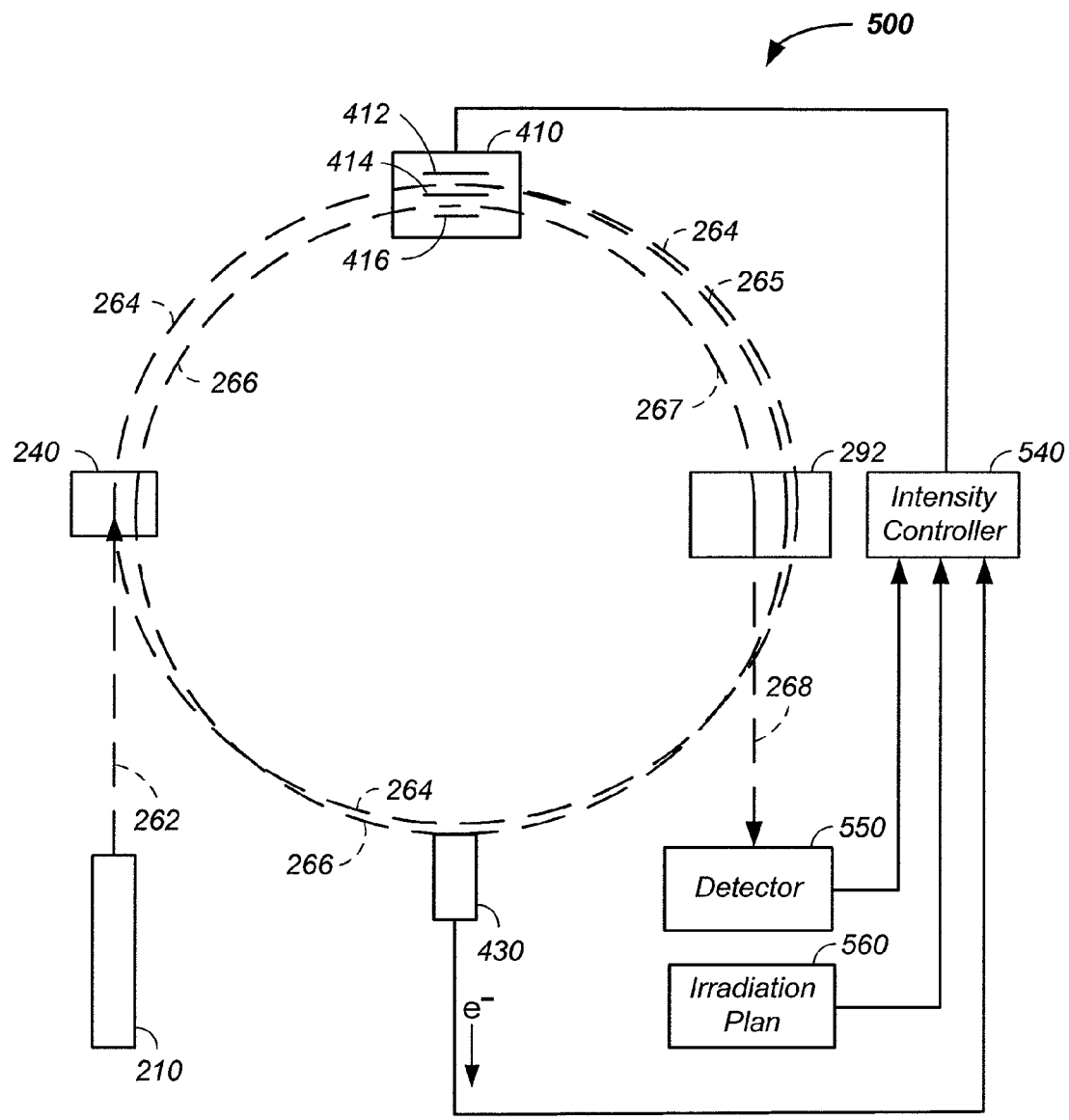
FIG. 5 illustrates a particle beam intensity control system.

Referring now to FIG. 5, typically when protons in the proton beam hit the material 430 electrons are given off. The resulting current is optionally measured and sent to the main controller 110 or to an intensity controller subsystem 540. The current is used as a measure of the circulating beam path intensity and is optionally used to control the RF cavity system. In one instance, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator. In another instance, the current is used as a feedback control to control the intensity of the extracted particle beam.

Referring still to FIG. 5, a feedback loop is added to the extraction system described supra. When protons in the proton beam hit the material 430 electrons are given off resulting in a current. The resulting current is converted to a voltage and is used as part of a ion beam intensity monitoring system or as part of an ion beam feedback loop for controlling beam intensity. The voltage is optionally measured and sent to the main controller 110 or to the controller subsystem 410. More particularly, when protons in the charged particle beam path pass through the material 430, some of the protons lose a small fraction of their energy, such as about one-tenth of a percent, which results in a secondary electron. That is, protons in the charged particle beam push some electrons when passing through material 430 giving the electrons enough energy to cause secondary emission. The resulting electron flow results in a current or signal that is proportional to the number of protons going through the target material 430. The resulting current is preferably converted to voltage and amplified. The resulting signal is referred to as a measured intensity signal.

The amplified signal or measured intensity signal resulting from the protons passing through the material 430 is preferably used in controlling the intensity of the extracted protons. For example, the measured intensity signal is compared to a goal signal, which is predetermined in an irradiation of the tumor plan 560. The difference between the measured intensity signal and the planned for goal signal is calculated. The difference is used as a control to the RF generator. Hence, the measured flow of current resulting from the protons passing through the material 430 is used as a control in the RF generator to increase or decrease the number of protons undergoing betatron oscillation and striking the material 430. Hence, the voltage determined off of the material 430 is used as a measure of the orbital path and is used as a feedback control to control the RF cavity system. Alternatively, the measured intensity signal is not used in the feedback control and is just used as a monitor of the intensity of the extracted protons.

As described, supra, the photons striking the material 430 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable.

For example, protons initially move at an equilibrium trajectory in the synchrotron 130. An RF field is used to excite the protons into a betatron oscillation. In one case, the frequency of the protons orbit is about 10 MHz. In one example, in about one millisecond or after about 10,000 orbits, the first protons hit an outer edge of the target material 430. The specific frequency is dependent upon the period of the orbit. Upon hitting the material 430, the protons push electrons through the foil to produce a current. The current is converted to voltage and amplified to yield a measured intensity signal. The measured intensity signal is used as a feedback input to control the applied RF magnitude, RF frequency, or RF field. Preferably, the measured intensity signal is compared to a target signal and a measure of the difference between the measured intensity signal and target signal is used to adjust the applied RF field in the RF cavity system 510 in the extraction system to control the intensity of the protons in the extraction step. Stated again, the signal resulting from the protons striking and/or passing through the material 430 is used as an input in RF field modulation. An increase in the magnitude of the RF modulation results in protons hitting the foil or material 430 sooner. By increasing the RF, more protons are pushed into the foil, which results in an increased intensity, or more protons per unit time, of protons extracted from the synchrotron 130.

In another example, a detector 550 external to the synchrotron 130 is used to determine the flux of protons extracted from the synchrotron and a signal from the external detector is used to alter the RF field or RF modulation in the RF cavity system 510. Here the external detector generates an external signal, which is used in a manner similar to the measured intensity signal, described in the preceding paragraphs. Particularly, the measured intensity signal is compared to a desired signal from the irradiation plan 560 in a feedback intensity controller 540, which adjusts the RF field between the first plate 412 and the second plate 414 in the extraction process, described supra.

In yet another example, when a current from material 430 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller 110 simultaneously controls the intensity control system to yield an extracted proton beam with controlled energy and controlled intensity where the controlled energy and controlled intensity are independently variable. Thus, the radiation spot hitting the tumor is under independent control of:

time;
energy;
intensity;
x-axis position, where the x-axis represents horizontal movement of the proton beam relative to the patient; and/or
y-axis position, where the y-axis represents vertical movement of the proton beam relative to the patient.

In addition, the patient is optionally independently translated and/or rotated relative to a translational axis of the proton beam at the same time.

Timing

In yet another embodiment of the invention, the main controller 110 controls timing of extraction. For example, extraction is in synchronization with patient respiration or breathing. For instance, extraction is performed when the patient is at the bottom of a breath so that the proton beam is generated when the internal organs, bones, and structures of the patient are in reproducible positions or are in reproducible relative positions. Accurate and precise delivery of protons to a tumor in body tissue is critical in charged particle beam therapy. Complicating accurate and precise deliver is natural movement of the body. Movement of the body occurs on multiple levels, including: (1) general patient movement, such as walking; (2) standing, sitting, or lying position variation; and (3) relative movement of internal body parts, such as organs. All of these movements change with time. Hence, the method of timing extraction of the proton beam results in enhanced targeting, precision, and/or accuracy of the delivered proton beam to the tumor of the patient.

Proton Energy and Intensity Control

Figure 6:
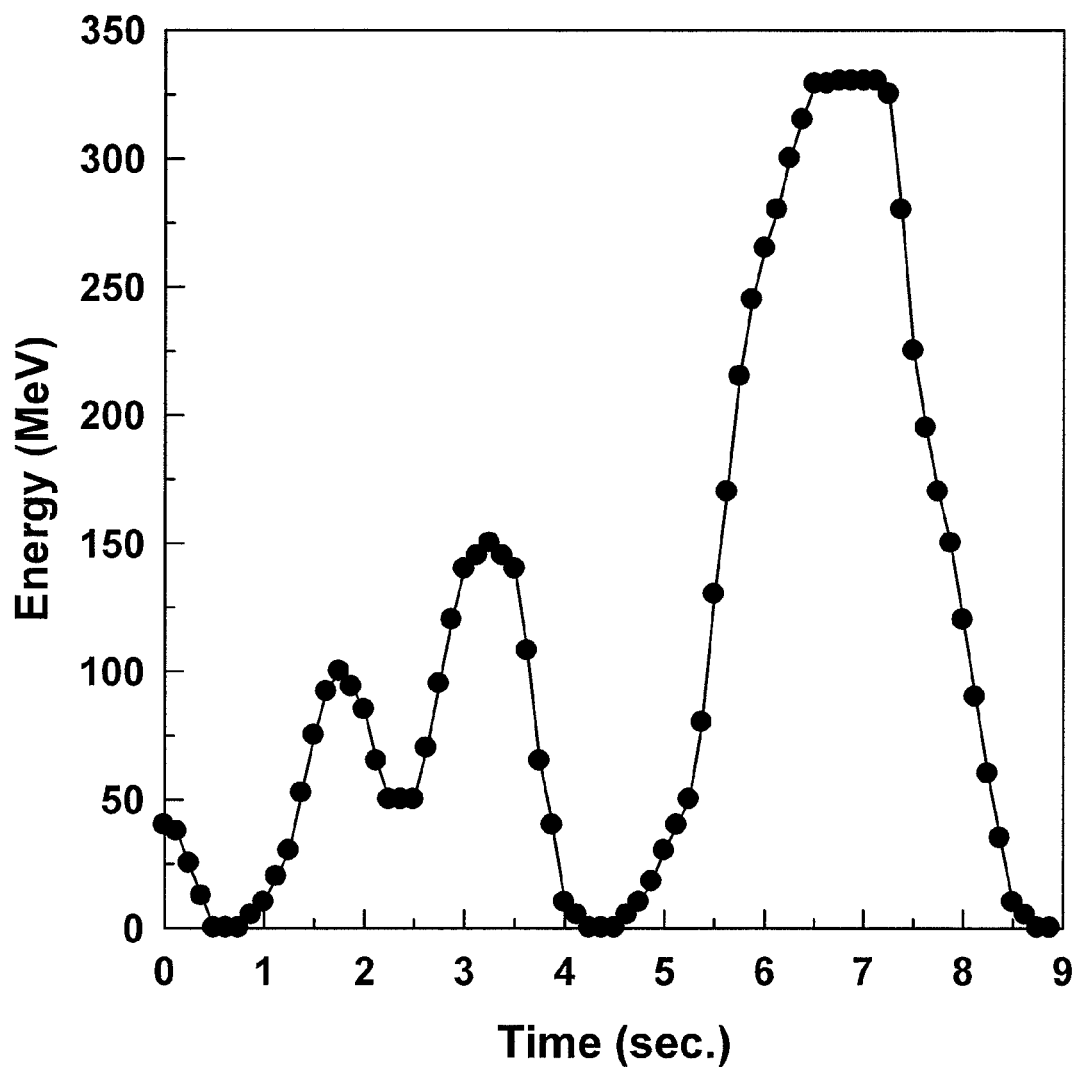
FIG. 6 demonstrates beam acceleration.
Figure 7:
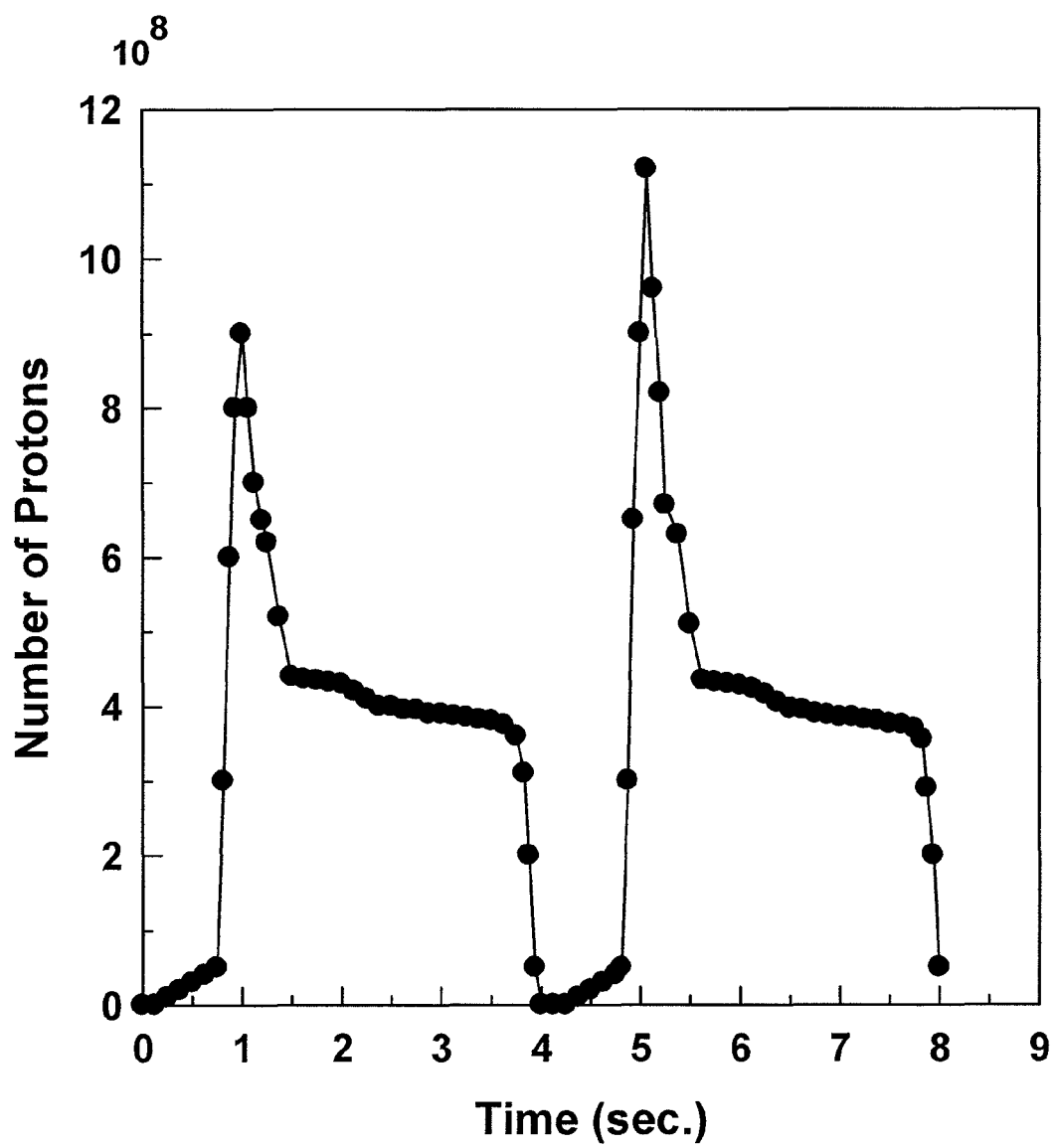
FIG. 7 demonstrates beam intensity.

Referring now to FIGS. 6 and 7, proton energy and intensity capabilities of the proton delivery system are demonstrated. Referring now to FIG. 6, beam acceleration up to a maximum energy of 330 MeV is demonstrated. Further illustrated is a flexible repeated acceleration and retardation of the proton beam in one cycle. Particularly, in the first cycle from the first to fourth seconds, the beam is accelerated to 100 MeV, retarded to 50 MeV and accelerated once more to 150 MeV. In the next cycle starting at the fifth second, the proton energy is increased rapidly to 330 MeV where it is maintained for one second, which is needed for carrying out tomography. Referring now to FIG. 7, the corresponding beam intensity is provided for the two serial cycles of the synchrotron accelerator's work. From approximately the 1½ to 3½ second marks, the beam is directed to a certain irradiating point. Upon achieving the necessary dose value, the extraction is interrupted, the beam is moved to the next point and the extraction process is resumed from the 5½ to 7½ second marks. Combined, FIGS. 6 and 7 demonstrate independent control of energy and intensity. FIGS. 6 and d7 are demonstrative in nature. In real time operation, each of the above described processes optionally are generated at ten times the demonstrated rate.

Proton Beam Position Control

Figure 8A:
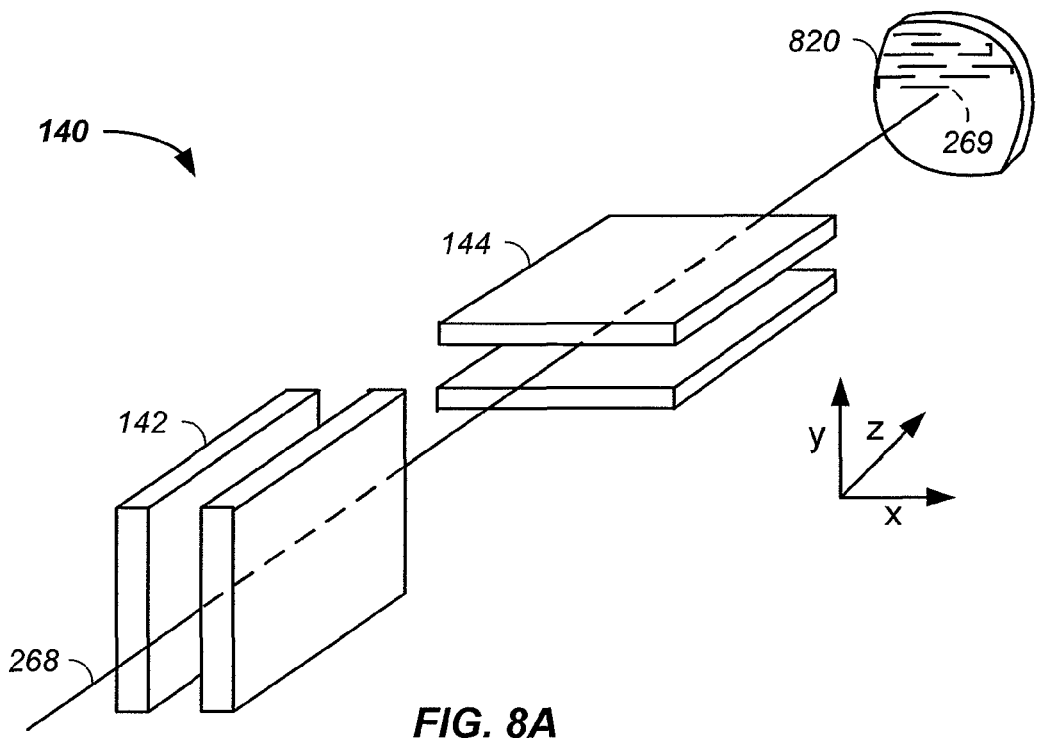
FIG. 8A illustrates charged particle treatment of a tumor in a patient and FIG. 8B illustrates 3-dimensional scanning of the charged particle beam.

Referring now to FIG. 8, a beam delivery and tissue volume scanning system is illustrated. Presently, the worldwide radiotherapy community uses a method of dose field forming using a pencil beam scanning system. In stark contrast, FIG. 8 illustrates a spot scanning system or tissue volume scanning system. In the tissue volume scanning system, the proton beam 268 is controlled, in terms of transportation and distribution, using an inexpensive and precise scanning system. The scanning system is an active system, where the beam is focused into a spot focal point of about one-half, one, two, or three millimeters in diameter in the tumor 820. The focal point is translated to a momentary position 269 along two axes while simultaneously altering the applied energy of the proton beam, which effectively changes the third dimension of the focal point. For example, in the illustrated system in FIG. 8A, the spot is moved horizontally, is translated down a vertical axis, and then is moved again horizontally. In this example, current is used to control a vertical scanning system having at least one magnet. The applied current alters the magnetic field of the vertical scanning system to control the vertical deflection of the proton beam. Similarly, a horizontal scanning magnet system controls the horizontal deflection of the proton beam. The degree of transport along each axes is controlled to conform to the tumor cross-section at the given depth. The depth is controlled by changing the energy of the proton beam. For example, the proton beam energy is decreased, so as to define a new penetration depth, and the scanning process is repeated along the horizontal and vertical axes covering a new cross-sectional area of the tumor.

The system has five axes of control: x-axis, y-axis, energy, intensity, and time. The intensity control provided by the feedback current and the sub-controller 540 provides the fifth axis of intensity control. Combined, the five axes of control allow scanning or movement of the proton beam focal point over the entire volume of the cancerous tumor. The time at each spot and the direction into the body for each spot is controlled to yield the desired radiation does at each sub-volume of the cancerous volume while distributing energy hitting outside of the tumor.

The focused beam spot volume dimension is preferably tightly controlled to a diameter of about 0.5, 1, or 2 millimeters, but is alternatively several centimeters in diameter. Preferred design controls allow scanning in two directions with: (1) a vertical amplitude of about 100 mm amplitude and frequency up to 200 Hz; and (2) a horizontal amplitude of about 700 mm amplitude and frequency up to 1 Hz. More or less amplitude in each axis is possible by altering the scanning magnet systems.

Figure 8B:
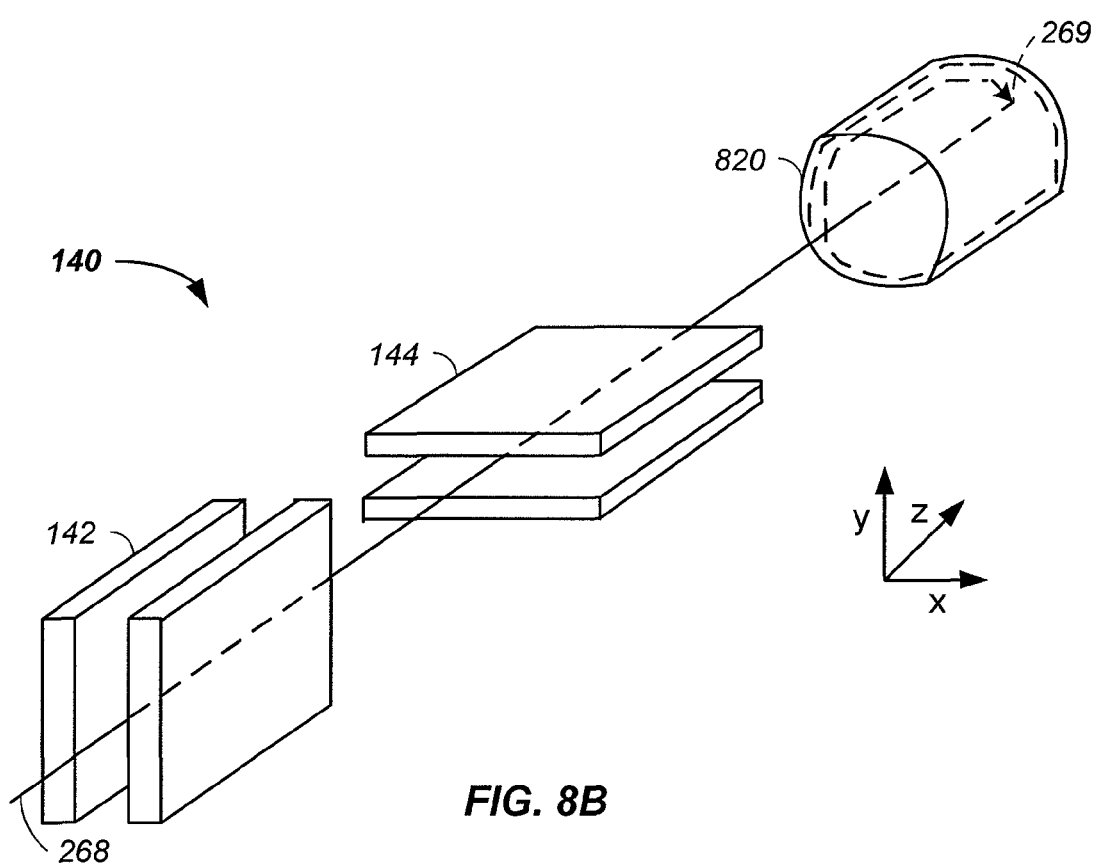

In FIG. 8B, the proton beam goes along a z-axis controlled by the beam energy, the horizontal movement is an x-axis, and the vertical direction is a y-axis. The distance the protons move along the z-axis into the tissue, in this example, is controlled by the kinetic energy of the proton. This coordinate system is arbitrary and exemplary. The actual control of the proton beam is controlled in 3-dimensional space using two scanning magnet systems and by controlling the kinetic energy of the proton beam.

Respiration Control

Accurate and precise delivery of protons to a tumor in body tissue is critical in charged particle beam therapy of tumors. Complicating accurate and precise deliver is natural movement of the body. One form or movement of the body is related to respiration of the patient, which results in movements throughout the body and especially in the chest cavity of the patient. The movement results in relative movement of internal body parts, such as organs, as a function of time. Hence, a method of determining position of elements of the body at and/or in close proximity in time to the charged particle therapy is needed. Herein, patient respiration monitoring and/or control methods and apparatus used in conjunction with charged particle therapy are described. Particularly, a patient respiration monitoring and/or control method and apparatus used in conjunction with multi-axis charged particle or proton beam radiation therapy of cancerous tumors is described. For example, the respiration monitoring system uses thermal and/or force sensors to determine where a patient is in a respiration cycle, optionally in combination with a feedback signal control delivered to the patient to inform the patient when breath control is required. The resulting breath control is timed with charged particle delivery to the tumor to enhance accuracy, precision, and efficiency of tumor treatment.

Figure 9:
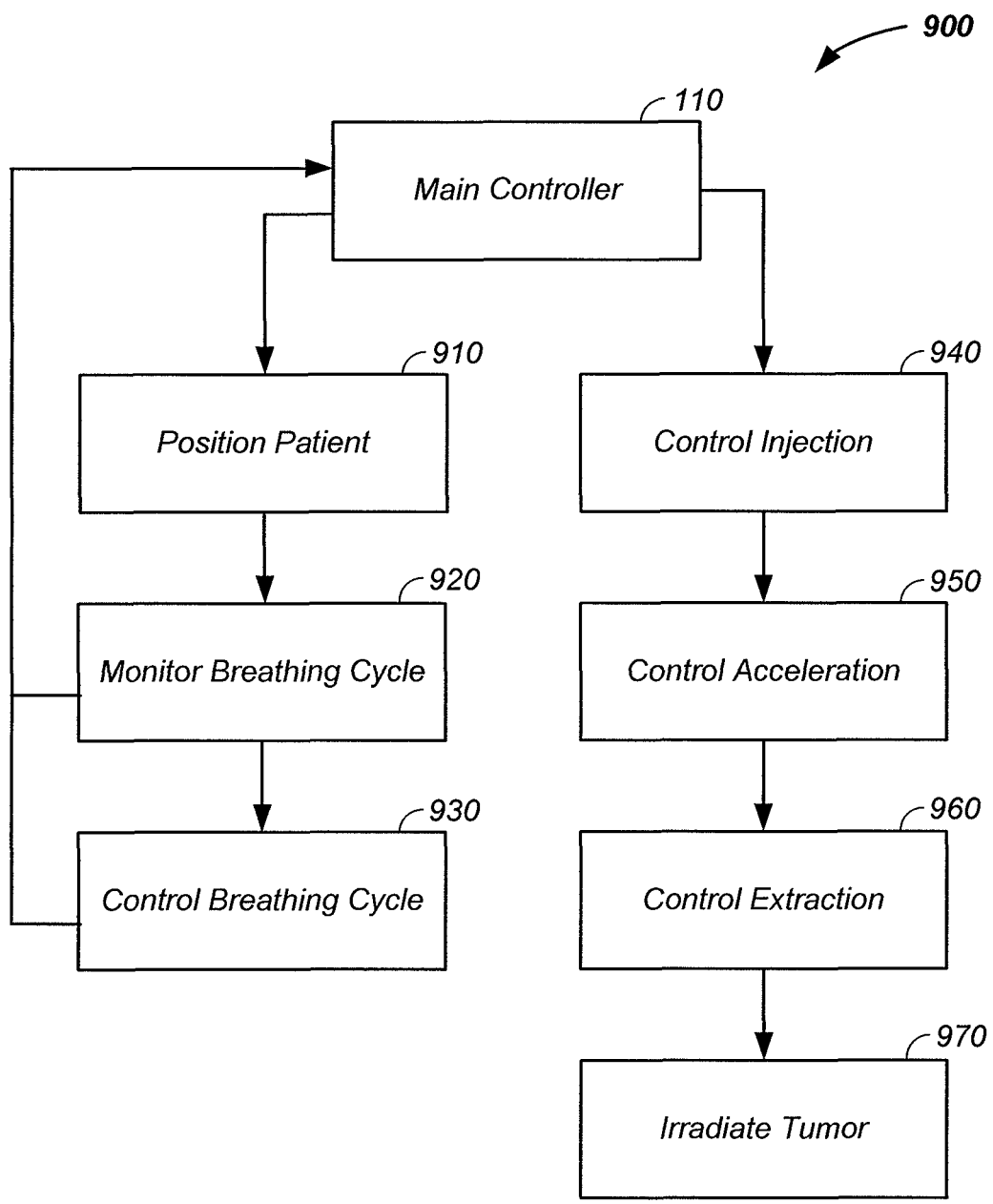
FIG. 9 illustrates tumor irradiation timed to respiration.

Referring now to FIG. 9, timing of proton delivery to the tumor based on the patient's respiration 900 is described. In one example, a patient is positioned 910 and once the rhythmic pattern of the subject's breathing or respiration cycle is determined 920, a signal is optionally delivered to the patient, such as via the display monitor, to more precisely control the breathing frequency 930. For example, the display screen is placed in front of the patient and a message or signal is transmitted to the display screen directing the subject when to hold their breath and when to breathe. Typically, a respiration control module uses input from one or more of the breathing sensors, described infra. For example, the input is used to determine when the next breath exhale is to complete. At the bottom of the breath, the control module displays a hold breath signal to the subject, such as on a monitor, via an oral signal, digitized and automatically generated voice command, or via a visual control signal. Preferably, a display monitor is positioned in front of the subject and the display monitor displays breathing commands to the subject. Typically, the subject is directed to hold their breath for a short period of time, such as about ½, 1, 2, 3, 5, or 10 seconds.

The period of time the breath is held is preferably synchronized to the delivery time of the proton beam to the tumor, which is about ½, 1, 2, or 3 seconds. While delivery of the protons at the bottom of the breath is preferred, protons are optionally delivered at any point in the respiration cycle, such as upon full inhalation. Delivery at the top of the breath or when the patient is directed to inhale deeply and hold their breath by the breathing control module is optionally performed as at the top of the breath the chest cavity is largest and for some tumors the distance between the tumor and surrounding tissue is maximized or the surrounding tissue is rarefied as a result of the increased volume. Hence, protons hitting surrounding tissue is minimized. Optionally, the display screen tells the patient when they are about to be asked to hold their breath, such as with a 3, 2, 1, second countdown so that the patient is aware of the task they are about to be asked to perform.

Respiration Sensors

A first example of a respiration monitoring system is provided. In a thermal respiration monitoring system, a sensor is placed by the nose and/or mouth of the patient. To avoid steric interference of the thermal sensor system components with proton therapy, the thermal breath monitoring system is preferably used when treating a tumor not located in the head or neck, such as a when treating a tumor in the torso or limbs. In the thermal monitoring system, a first thermal resistor is used to monitor the patient's respiration cycle and/or location in the patient's respiration cycle. Preferably, the first thermal resistor is placed by the patient's nose, such that the patient exhaling through their nose onto the first thermal resistor warms the first thermal resistor indicating an exhale. Preferably, a second thermal resistor operates as an environmental temperature sensor. The second thermal resistor is preferably placed out of the exhalation path of the patient but in the same local room environment as the first thermal resistor. Generated signal, such as current from the thermal resistors, is preferably converted to voltage and communicated with the main controller 110 or a sub-controller of the main controller. Preferably, the second thermal resistor is used to adjust for the environmental temperature fluctuation that is part of a signal of the first thermal resistor, such as by calculating a difference between the values of the thermal resistors, to yield a more accurate reading of the patient's breathing cycle.

A second example of a monitoring system is provided. In an example of a force breath monitoring system, a sensor is placed by the torso. To avoid steric interference of the force sensor system components with proton therapy, the force breath monitoring system is preferably used when treating a tumor located in the head, neck, or limbs. In the force monitoring system, a belt or strap is placed around an area of the patient's torso that expands and contracts with each breath cycle of the patient. The belt is preferably tight about the patient's chest and is flexible. A force meter is attached to the belt and senses the patients respiration pattern. The forces applied to the force meter correlate with periods of the breathing cycle. The signals from the force meter are preferably communicated with the main controller 110 or a sub-controller of the main controller.

Proton Beam Therapy Synchronization with Respiration

In one embodiment, charged particle therapy and preferably multi-field proton therapy is coordinated and synchronized with patient respiration via use of the respiration feedback sensors, described supra, used to monitor and/or control patient respiration. Preferably, the charged particle therapy is performed on a patient in a partially immobilized and repositionable position and the proton delivery to the tumor is timed to patient respiration via control of charged particle beam injection, acceleration, extraction, and/or targeting methods and apparatus. The synchronization enhances proton delivery accuracy by removing position ambiguity due to the relative movement of body constituents during a patient respiration cycle.

In a second embodiment, an X-ray system is used to provide X-ray images of a patient in the same orientation as viewed by a proton therapy beam and both the X-ray system and the proton therapy beam are synchronized with patient respiration. Preferably, the synchronized system is used in conjunction with the negative ion beam source, synchrotron, and/or targeting method and apparatus to provide an X-ray timed with patient breathing where the X-ray is collected immediately prior to and/or concurrently with particle beam therapy irradiation to ensure targeted and controlled delivery of energy relative to a patient position resulting in efficient, precise, and/or accurate treatment of a solid cancerous tumor with minimization of damage to surrounding healthy tissue in a patient using the proton beam position verification system.

Referring again to FIG. 9, a proton delivery control algorithm is used to synchronize delivery of the protons to the tumor within a given period of each breath, such as at the top of a breath, at the bottom of a breath, and/or when the subject is holding their breath. The proton delivery control algorithm is preferably integrated with the respiration control module. Thus, the proton delivery control algorithm knows when the subject is breathing, where in the respiration cycle the subject is, and/or when the subject is holding their breath. Based on monitoring the patient's respiration 920 or controlling the patient's respiration 930, the proton delivery control algorithm or main controller 110 controls timing of proton delivery. For example, the main controller 110 controls when protons are injected 940 and/or inflected into the synchrotron, how the protons are accelerated 950, when a radio frequency signal is applied to induce an oscillation, as described supra, and when a direct current voltage is applied to extract protons 960 from the synchrotron, as described supra. Hence, the tumor is irradiated 970 at a known or controlled point in the patient's respiration cycle, thereby enhancing precision and accuracy of proton delivery to the tumor. Typically, the proton delivery control algorithm initiates proton inflection and subsequent radio frequency induced oscillation before the subject is directed to hold their breath or before the identified period of the breathing cycle selected for a proton delivery time. In this manner, the proton delivery control algorithm delivers protons at a selected period of the respiration cycle by simultaneously or nearly simultaneously delivering the high direct current voltage to the second pair of plates, described supra, which results in extraction of the protons from the synchrotron and subsequent delivery to the subject at the selected time point. Since the period of acceleration of protons in the synchrotron is constant or known for a desired energy level of the proton beam, the proton delivery control algorithm is used to set an alternating current RF signal that matches the breathing cycle or directed breathing cycle of the subject.

Figure 10:
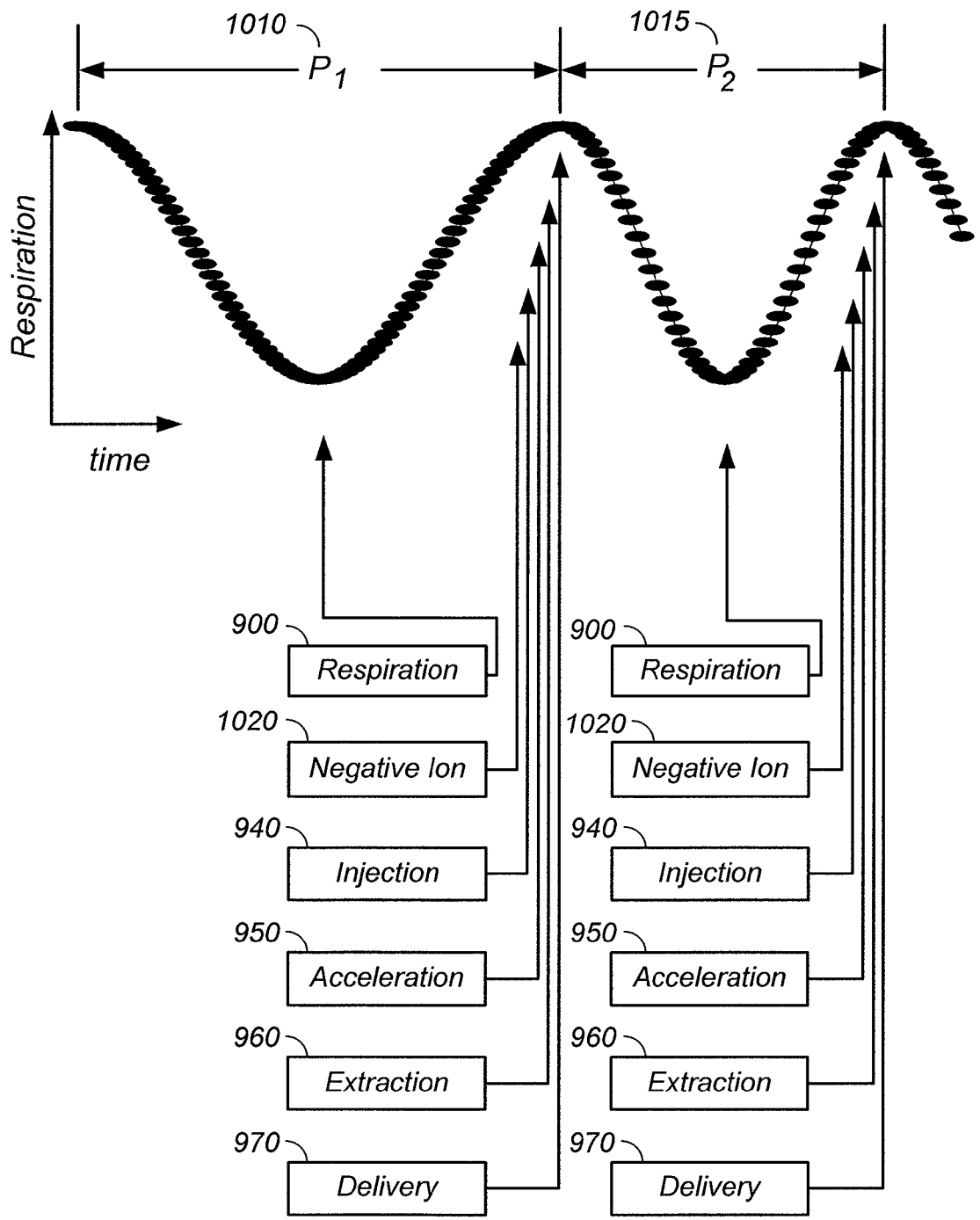
FIG. 10 illustrates charged particle delivery synchronized to variable respiration rates.

Referring now to FIG. 10, an example is used to clarify the magnetic field control using a feedback loop to change delivery times and/or periods of proton pulse delivery. In one case, a respiration sensor senses the respiration cycle of the patient. Optionally, the respiration sensor sends the patient's breathing pattern or information to an algorithm in the magnetic field controller, typically via the patient interface module 150 and/or via the main controller 110 or a subcomponent thereof. The algorithm predicts and/or measures when the patient is at a particular point in the breathing cycle, such as at the top or bottom of a breath. One or more magnetic field sensors are used as inputs to the magnetic field controller, which controls a magnet power supply for a given magnetic, such as within a first turning magnet 240 of a synchrotron 130. The control feedback loop is thus used to dial the synchrotron to a selected energy level and to deliver protons with the desired energy at a selected point in time, such as at a particular point in the respiration cycle. The selected point in the respiration cycle is optionally anywhere in the respiration cycle and/or for any duration during the respiration cycle. As illustrated in FIG. 10, the selected time period is at the top of a breath for a period of about 0.1, 0.5, or 1 second. More particularly, the main controller 110 controls injection of hydrogen into the injection system, formation of the negative ion 1020, controls extraction of negative ions from a negative ion source, controls injection 940 of protons into the synchrotron 130, and/or controls acceleration 950 of the protons in a manner that combined with extraction 960 delivers 970 the protons 268 to the tumor at a selected point in the respiration cycle. Intensity of the proton beam is also selectable and controllable by the main controller 110 at this stage, as described supra. The feedback control from the magnetic field controller is optionally to a power or power supplies for one or both of the main bending magnet 250 or to the correction coils 380, 390 within the main bending magnet 250. Having smaller applied currents, the correction coils 380, 390 are rapidly adjustable to a newly selected acceleration frequency or corresponding charged particle energy level. Particularly, the magnetic field controller alters the applied fields to the main bending magnets or correction coils that are tied to the patient's respiration cycle. This system is in stark contrast to a system where the current is stabilized and the synchrotron delivers pulses with a fixed period. Preferably, the feedback of the magnetic field design coupled with the correction coils allows for the extraction cycle to match the varying respiratory rate of the patient, such as where a first respiration period 1010, $P_1$, does not equal a second respiration period 1015, $P_2$.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for extracting a circulating charged particle beam from a synchrotron, said synchrotron having a center, said apparatus comprising: an extraction material; at least a one kilovolt direct current field applied across a pair of extraction blades; a deflector; a patient respiration monitor generating a respiration signal; and a main controller, wherein the circulating charged particle beam passes through said extraction material resulting in a reduced energy charged particle beam, wherein the reduced energy charged particle beam passes between said pair of extraction blades, wherein the direct current field redirects the reduced energy charged particle beam through said deflector, wherein said deflector yields an extracted charged particle beam, wherein said extraction material comprises a foil less than about one hundred fifty micrometers thick, wherein a radio frequency voltage applied across a first pair of blades is configured to induce a betatron oscillation on the circulating charged particle beam, wherein a first distance between said center of said synchrotron and said pair of extraction blades is less than a second distance between said center of said synchrotron and said pair of first blades, wherein the circulating charged particle beam comprises a radius of curvature passing through said first pair of blades, wherein the reduced energy charged particle beam, resulting from transmission through said extraction material, comprises a radius of curvature passing through said extraction blades, wherein timing of the extracted charged particle beam is synchronized to said respiration signal, and said main controller timing all of: (1) particle beam injection, (2) particle beam acceleration, and (3) timing of said radio frequency voltage to synchronize with said respiration signal.

2. The apparatus of claim 1, wherein said extraction material consists essentially of atoms having six or fewer protons.

3. The apparatus of claim 2, wherein said deflector comprises a Lambertson magnet.

4. The apparatus of claim 1, wherein said extraction material comprises any of:
beryllium;
lithium hydride; and
carbon.

5. The apparatus of claim 1, wherein the circulating charged particle beam traverses said first pair of blades during acceleration.

6. The apparatus of claim 1, wherein an inner blade of said first pair of blades is in common with an outer blade of said pair of extraction blades.

7. The apparatus of claim 1, further comprising an intensity controller controlling intensity of the extracted charged particle beam via a feedback control.

8. The apparatus of claim 7, wherein an induced current results from the circulating charged particle beam passing through said extraction material, wherein the induced current comprises a feedback input to said intensity controller.

9. The apparatus of claim 1, wherein the extracted charged particle beam is synchronized in time to patient respiration using said respiration signal.

10. The apparatus of claim 1, further comprising an intensity controller controlling intensity of the extracted charged particle beam via a feedback control.

11. The apparatus of claim 10, wherein an induced current results from the circulating charged particle beam passing through said extraction material, wherein the induced current comprises a feedback input to said intensity controller.

12. The apparatus of claim 10, wherein said intensity controller alters an applied radio frequency inducing betatron oscillation on the circulating charged particle beam.

13. The apparatus of claim 1, further comprising at least one turning magnet.

14. The apparatus of claim 13, wherein said turning magnet comprises a magnetic field concentrating first magnet, wherein said first magnet comprises:
   a gap through which the circulating charged particle beam circulates;
   a first cross-section diameter not in contact with said gap; and
   a second cross-sectional diameter proximate said gap, wherein said second cross-section diameter is less than seventy percent of said first cross-sectional diameter, wherein a magnetic field passing through said first cross-sectional diameter concentrates in said second cross-sectional diameter before crossing said gap.

15. An apparatus for extracting a circulating charged particle beam from a synchrotron, said synchrotron having a center, said apparatus comprising:
   an extraction material;
   at least a one kilovolt direct current field applied across a pair of extraction blades;
   a deflector,
   wherein the circulating charged particle beam passes through said extraction material resulting in a reduced energy charged particle beam,
   wherein the reduced energy charged particle beam passes between said pair of extraction blades,
   wherein the direct current field redirects the reduced energy charged particle beam through said deflector,
   wherein said deflector yields an extracted charged particle beam,
   wherein said extraction material comprises any of:
      beryllium;
      lithium hydride; and
      carbon, and
   wherein said extraction material comprises a foil of about thirty to one hundred micrometers thickness.

16. The apparatus of claim 15, further comprising a main controller, said main controller timing all of:
   (1) particle beam injection,
   (2) particle beam acceleration, and
   (3) timing of said radio frequency voltage to synchronize with said respiration signal.

17. A method for extracting a circulating charged particle beam from a synchrotron, comprising the steps of:
   transmitting the circulating charged particle beam through an extraction material, said extraction material yielding a reduced energy charged particle beam,
   wherein said extraction material comprises any of:
      beryllium;
      lithium hydride; and
      carbon, and
   wherein said extraction material comprises a foil of about forty to sixty microns thickness;
   applying at least five hundred volts across a first pair of blades; and
   passing the reduced energy charged particle beam between said first pair of blades,
   wherein said first pair of blades redirect the reduced energy charged particle beam to a deflector, and
   wherein said deflector yields an extracted charged particle beam.

18. The method of claim 17, wherein said extraction material consists essentially of atoms having six or fewer protons.

19. The method of claim 17, further comprising the step of:
   inducing betatron oscillation using a second pair of blades, wherein the circulating charged particle beam passes between said second pair of blades prior to said step of transmitting.

20. The method of claim 17, further comprising the step of:
   applying a radio frequency voltage across a second pair of blades to alter the circulating path of the circulating charged particle beam.

21. The method of claim 17, wherein a first distance between said center of said synchrotron and said first pair of blades is less than a second distance between said center of said synchrotron and said second pair of blades,
   wherein the circulating charged particle beam comprises a second radius of curvature passing through said second pair of blades,
   wherein the reduced energy charged particle beam, resulting from transmission through said extraction material, comprises a first radius of curvature passing through said first pair of blades
   wherein said reduced energy charged particle beam exits said synchrotron within an inner diameter of said circulating charged particle beam.

22. The method of claim 21, further comprising the step of:
   controlling intensity of the extracted charged particle beam with an intensity controller using a feedback control.

23. The method of claim 22, wherein an induced current results from the circulating charged particle beam passing through said extraction material, wherein the induced current comprises a feedback input to said step of controlling intensity.

24. The method of claim 17, further comprising the step of:
   controlling intensity of the extracted charged particle beam with an intensity controller using a feedback control.

25. The method of claim 24, wherein an induced current results from the circulating charged particle beam passing through said extraction material, wherein the induced current comprises a feedback input to said step of controlling intensity.

26. The method of claim 25, wherein said intensity controller alters duration of an applied radio frequency inducing altered trajectory of the circulating charged particle beam.

27. A method for extracting a circulating charged particle beam from a synchrotron, comprising the steps of:
   providing a turning magnet in said synchrotron, said turning magnet wound by a winding coil and a correction coil;
   providing a first current to said winding coil and a second current to said correction coil, said second current less than ten percent of said first current;

generating a feedback signal using a magnetic field sensor, said magnetic field sensor proximate said turning magnet;

stabilizing a magnetic field about said turning magnet using said feedback signal in control of said second current applied to said correction coil;

after said step of stabilizing the magnetic field, transmitting the circulating charged particle beam through an extraction material, said extraction material yielding a reduced energy charged particle beam;

applying a field of at least five hundred volts across a pair of extraction blades;

passing the reduced energy charged particle beam between said pair of extraction blades, wherein said field redirects the reduced energy charged particle as an extracted charged particle beam.

28. The method of claim 27, further comprising the step of: synchronizing said step of transmitting with a patient respiration signal.

29. The method of claim 27, further comprising the step of: prior to said step of transmitting, inducing betatron oscillation on the circulating charged particle beam, wherein said step of inducing occurs at a selected energy level of the circulating charged particle beam, wherein the betatron oscillation increases average radius of curvature of the circulating charged particle beam until said step of transmitting yields the reduced energy charged particle beam, wherein said step of inducing at said selected energy level yields an energy controlled extracted charged particle beam.

30. The method of claim 29, further comprising the step of: controlling intensity of the energy controlled extracted charged beam with an intensity controller.

31. The method of claim 30, wherein said step of controlling comprises the steps of:

inputting a feedback signal to said intensity controller, said step of transmitting yielding emitted electrons in the process of the circulating charged particle beam striking said extraction material, wherein the emitted electrons are converted to said feedback signal;

comparing said feedback signal to an irradiation plan intensity;

adjusting betatron oscillation with said intensity controller until said feedback signal proximately equals said irradiation plan intensity, wherein said energy controlled extracted charged particle beam comprises an independent intensity control.

32. The method of claim 27, further comprising the steps of:

inducing a change in radial movement of the circulating charged particle beam: (1) after acceleration of the charged particle beam to a selected energy and (2) prior to said step of transmitting the circulating charged particle beam through said extraction material; and controlling intensity of said extracted charged particle beam using an electron flow resultant from the charged particle beam transmitting through said extraction material.

33. The method of claim 32, wherein energy control of said extracted charged particle beam is independent of intensity control of said extracted charged particle beam.

* * * * *